(12) United States Patent
Vozila et al.

(10) Patent No.: US 11,531,807 B2
(45) Date of Patent: Dec. 20, 2022

(54) SYSTEM AND METHOD FOR CUSTOMIZED TEXT MACROS

(71) Applicant: Nuance Communications, Inc., Burlington, MA (US)

(72) Inventors: Paul Joseph Vozila, Arlington, MA (US); Joel Praveen Pinto, Aachen (DE); Frank Diehl, Aachen (DE)

(73) Assignee: Nuance Communications, Inc., Burlington, MA (US)

( * ) Notice: Subject to any disclaimer, the term of this patent is extended or adjusted under 35 U.S.C. 154(b) by 161 days.

(21) Appl. No.: 16/588,897

(22) Filed: Sep. 30, 2019

(65) Prior Publication Data

US 2020/0410045 A1 Dec. 31, 2020

Related U.S. Application Data

(60) Provisional application No. 62/868,474, filed on Jun. 28, 2019.

(51) Int. Cl.
*G06F 40/169* (2020.01)
*G06F 40/131* (2020.01)
(Continued)

(52) U.S. Cl.
CPC .......... *G06F 40/131* (2020.01); *G06F 40/169* (2020.01); *G10L 15/26* (2013.01); *G16H 15/00* (2018.01)

(58) Field of Classification Search
CPC ...... G06F 40/131; G06F 40/169; G06F 40/10; G06F 40/20; G06F 40/30; G06F 40/40; G10L 15/26; G16H 15/00; G06N 20/00
See application file for complete search history.

(56) References Cited

U.S. PATENT DOCUMENTS 5,805,747 A 9/1998 Bradford
5,809,476 A 9/1998 Ryan
(Continued)

FOREIGN PATENT DOCUMENTS

CN 101790752 A 7/2010
CN 106448722 A 2/2017
(Continued)

OTHER PUBLICATIONS

Final Office Action issued in related U.S. Appl. No. 16/059,974, dated Jul. 6, 2020.
(Continued)

*Primary Examiner* — Sanchita Roy
(74) *Attorney, Agent, or Firm* — Brian J. Colandreo; Michael T. Abramson; Holland & Knight LLP

(57) ABSTRACT

A method, computer program product, and computer system for encoding, by a computing device, a transcript and text macros into vector representations. A word by word report may be predicted based upon, at least in part, the encoding. An attention mechanism may be queried based upon, at least in part, a decoder state. An attention distribution may be produced over an encoder output. An interpolation of the encoder output may be produced based upon, at least in part, the attention distribution. The interpolation of the encoder output may be input into a decoder for report modeling that includes text macro location and content.

20 Claims, 8 Drawing Sheets

(51) Int. Cl.
*G16H 15/00* (2018.01)
*G10L 15/26* (2006.01)

(56) References Cited

U.S. PATENT DOCUMENTS

| | | |
|---|---|---|
| 5,940,118 A | 8/1999 | Van Schyndel |
| 5,970,455 A | 10/1999 | Wilcox |
| 5,970,457 A | 10/1999 | Brant et al. |
| 6,004,276 A | 12/1999 | Wright |
| 6,031,526 A | 2/2000 | Shipp |
| 6,266,635 B1 | 7/2001 | Sneh |
| 6,332,122 B1 | 12/2001 | Ortega et al. |
| 6,401,063 B1 | 6/2002 | Hebert et al. |
| 6,405,165 B1 | 6/2002 | Blum et al. |
| 6,434,520 B1 | 8/2002 | Kanevsky et al. |
| 6,523,166 B1 | 2/2003 | Mishra et al. |
| 6,589,169 B1 | 7/2003 | Surwit et al. |
| 6,801,916 B2 | 10/2004 | Roberge et al. |
| 6,823,203 B2 | 11/2004 | Jordan |
| 6,847,336 B1 | 1/2005 | Lemelson et al. |
| 6,915,254 B1 | 7/2005 | Heinze et al. |
| 7,236,618 B1 | 6/2007 | Chui et al. |
| 7,298,930 B1 | 11/2007 | Erol et al. |
| 7,412,396 B1 | 8/2008 | Haq |
| 7,493,253 B1 | 2/2009 | Ceusters et al. |
| 7,496,500 B2 | 2/2009 | Reed et al. |
| 7,516,070 B2 | 4/2009 | Kahn |
| 7,558,156 B2 | 7/2009 | Vook et al. |
| 7,817,805 B1 | 10/2010 | Griffin |
| 7,830,962 B1 | 11/2010 | Fernandez |
| 8,214,082 B2 | 7/2012 | Tsai et al. |
| 8,345,887 B1 | 1/2013 | Betbeder |
| 8,369,593 B2 | 2/2013 | Peng et al. |
| 8,589,177 B2 | 11/2013 | Haq |
| 8,589,372 B2 | 11/2013 | Krislov |
| 8,606,594 B2 | 12/2013 | Stern et al. |
| 8,661,012 B1 | 2/2014 | Baker et al. |
| 8,843,372 B1 | 9/2014 | Isenberg |
| 8,983,889 B1 | 3/2015 | Stoneman |
| 9,146,301 B2 | 9/2015 | Adcock et al. |
| 9,224,180 B2 | 12/2015 | Macoviak et al. |
| 9,270,964 B1 | 2/2016 | Tseytlin |
| 9,293,151 B2 | 3/2016 | Herbig et al. |
| 9,326,143 B2 | 4/2016 | McFarland |
| 9,338,493 B2 | 5/2016 | Van Os et al. |
| 9,536,049 B2 | 1/2017 | Brown et al. |
| 9,536,106 B2 | 1/2017 | Fram |
| 9,569,593 B2 | 2/2017 | Casella dos Santos |
| 9,569,594 B2 | 2/2017 | Casella dos Santos |
| 9,668,006 B2 | 5/2017 | Betts et al. |
| 9,668,024 B2 | 5/2017 | Os et al. |
| 9,668,066 B1 | 5/2017 | Betts et al. |
| 9,679,102 B2 | 6/2017 | Cardoza et al. |
| 9,779,631 B1 | 10/2017 | Miller et al. |
| 9,785,753 B2 | 10/2017 | Casella dos Santos |
| 9,799,206 B1 | 10/2017 | Wilson Van Horn |
| 9,824,691 B1 | 11/2017 | Montero et al. |
| RE47,049 E | 9/2018 | Zhu |
| 10,090,068 B2 | 10/2018 | Kusens et al. |
| 10,219,083 B2 | 2/2019 | Farmani et al. |
| 10,423,948 B1 | 9/2019 | Wilson et al. |
| 10,440,498 B1 | 10/2019 | Amengual Gari et al. |
| 10,491,598 B2 | 11/2019 | Leblang et al. |
| 10,559,295 B1 | 2/2020 | Abel |
| 10,693,872 B1 | 6/2020 | Larson et al. |
| 10,719,222 B2 | 7/2020 | Strader |
| 10,785,565 B2 | 9/2020 | Mate et al. |
| 10,810,574 B1 | 10/2020 | Wilson et al. |
| 10,972,682 B1 | 4/2021 | Muenster |
| 11,216,480 B2 | 1/2022 | Oz et al. |
| 11,222,103 B1 | 1/2022 | Gallopyn et al. |
| 11,222,716 B2 | 1/2022 | Vozila et al. |
| 11,227,588 B2 | 1/2022 | Wolff et al. |
| 11,227,679 B2 | 1/2022 | Owen et al. |
| 11,238,226 B2 | 2/2022 | Vozila et al. |
| 11,250,382 B2 | 2/2022 | Sharma et al. |
| 11,250,383 B2 | 2/2022 | Sharma et al. |
| 11,257,576 B2 | 2/2022 | Owen et al. |
| 11,270,261 B2 | 3/2022 | Vozila |
| 2001/0029322 A1 | 10/2001 | Iliff |
| 2001/0041992 A1 | 11/2001 | Lewis et al. |
| 2001/0042114 A1 | 11/2001 | Agraharam et al. |
| 2002/0032583 A1 | 3/2002 | Joao |
| 2002/0069056 A1 | 6/2002 | Nofsinger |
| 2002/0072896 A1 | 6/2002 | Roberge et al. |
| 2002/0082825 A1 | 6/2002 | Rowlandson et al. |
| 2002/0143533 A1 | 10/2002 | Lucas et al. |
| 2002/0170565 A1 | 11/2002 | Walker et al. |
| 2002/0178002 A1 | 11/2002 | Boguraev et al. |
| 2002/0194005 A1 | 12/2002 | Lahr |
| 2003/0028401 A1 | 2/2003 | Kaufman et al. |
| 2003/0105638 A1 | 6/2003 | Taira |
| 2003/0125940 A1 | 7/2003 | Basson et al. |
| 2003/0154085 A1 | 8/2003 | Kelley |
| 2003/0185411 A1 | 10/2003 | Atlas et al. |
| 2003/0216937 A1 | 11/2003 | Schreiber et al. |
| 2004/0078228 A1 | 4/2004 | Fitzgerald et al. |
| 2004/0122701 A1 | 6/2004 | Dahlin et al. |
| 2004/0128323 A1 | 7/2004 | Walker |
| 2004/0162728 A1 | 8/2004 | Thomson et al. |
| 2004/0167644 A1 | 8/2004 | Swinney |
| 2004/0172070 A1 | 9/2004 | Moore et al. |
| 2004/0186712 A1 | 9/2004 | Coles et al. |
| 2004/0243545 A1 | 12/2004 | Boone et al. |
| 2004/0247016 A1 | 12/2004 | Faries, Jr. et al. |
| 2005/0055215 A1 | 3/2005 | Klotz |
| 2005/0075543 A1 | 4/2005 | Calabrese |
| 2005/0114179 A1 | 5/2005 | Brackett et al. |
| 2005/0165285 A1 | 7/2005 | Liff |
| 2005/0192848 A1 | 9/2005 | Kozminski et al. |
| 2006/0041427 A1 | 2/2006 | Yegnanarayanan et al. |
| 2006/0041428 A1 | 2/2006 | Fritsch et al. |
| 2006/0061595 A1 | 3/2006 | Goede |
| 2006/0074656 A1 | 4/2006 | Mathias et al. |
| 2006/0092978 A1 | 5/2006 | John et al. |
| 2006/0104454 A1 | 5/2006 | Guitarte Perez et al. |
| 2006/0104458 A1 | 5/2006 | Kenoyer et al. |
| 2006/0142739 A1 | 6/2006 | DiSilestro et al. |
| 2006/0173753 A1 | 8/2006 | Padmanabhan et al. |
| 2006/0241943 A1 | 10/2006 | Benja-Athon et al. |
| 2006/0277071 A1 | 12/2006 | Shufeldt |
| 2007/0033032 A1 | 2/2007 | Schubert et al. |
| 2007/0071206 A1 | 3/2007 | Gainsboro et al. |
| 2007/0136218 A1 | 6/2007 | Bauer et al. |
| 2007/0167709 A1 | 7/2007 | Slayton et al. |
| 2007/0169021 A1 | 7/2007 | Huynh et al. |
| 2007/0208567 A1 | 9/2007 | Amento et al. |
| 2007/0233488 A1 | 10/2007 | Carus et al. |
| 2007/0260977 A1 | 11/2007 | Allard et al. |
| 2008/0004505 A1 | 1/2008 | Kapit et al. |
| 2008/0004904 A1 | 1/2008 | Tran |
| 2008/0040162 A1 | 2/2008 | Brice |
| 2008/0059182 A1 | 3/2008 | Benja-Athon et al. |
| 2008/0062280 A1 | 3/2008 | Wang et al. |
| 2008/0071575 A1 | 3/2008 | Climax et al. |
| 2008/0177537 A1 | 7/2008 | Ash et al. |
| 2008/0240463 A1 | 10/2008 | Florencio et al. |
| 2008/0247274 A1 | 10/2008 | Seltzer et al. |
| 2008/0263451 A1 | 10/2008 | Portele et al. |
| 2009/0024416 A1 | 1/2009 | McLaughlin et al. |
| 2009/0055735 A1 | 2/2009 | Zaleski et al. |
| 2009/0070103 A1 | 3/2009 | Beggelman et al. |
| 2009/0076855 A1 | 3/2009 | McCord |
| 2009/0089100 A1 | 4/2009 | Nenov et al. |
| 2009/0136094 A1 | 5/2009 | Driver |
| 2009/0150771 A1 | 6/2009 | Buck et al. |
| 2009/0172773 A1 | 7/2009 | Moore |
| 2009/0177477 A1 | 7/2009 | Nenov |
| 2009/0177492 A1 | 7/2009 | Hasan et al. |
| 2009/0178144 A1 | 7/2009 | Redlich |
| 2009/0187407 A1* | 7/2009 | Soble .................. G10L 15/26 704/260 |
| 2009/0198520 A1 | 8/2009 | Piovanetti-Perez |
| 2009/0213123 A1 | 8/2009 | Crow |

(56) References Cited

U.S. PATENT DOCUMENTS

| | | |
|---|---|---|
| 2009/0259136 A1 | 10/2009 | Schieb |
| 2009/0270690 A1 | 10/2009 | Roos et al. |
| 2010/0036676 A1 | 2/2010 | Safdi et al. |
| 2010/0039296 A1 | 2/2010 | Marggraff et al. |
| 2010/0076760 A1 | 3/2010 | Kraenzel et al. |
| 2010/0076784 A1 | 3/2010 | Greenburg et al. |
| 2010/0077289 A1 | 3/2010 | Das et al. |
| 2010/0082657 A1 | 4/2010 | Paprizos et al. |
| 2010/0088095 A1 | 4/2010 | John |
| 2010/0094650 A1 | 4/2010 | Tran |
| 2010/0094656 A1 | 4/2010 | Conant |
| 2010/0094657 A1 | 4/2010 | Stern et al. |
| 2010/0100376 A1 | 4/2010 | Harrington |
| 2010/0131532 A1 | 5/2010 | Schultz |
| 2010/0145736 A1 | 6/2010 | Rohwer |
| 2010/0223216 A1 | 9/2010 | Eggert et al. |
| 2010/0238323 A1 | 9/2010 | Englund |
| 2010/0241662 A1 | 9/2010 | Keith, Jr. |
| 2011/0015943 A1 | 1/2011 | Keldie et al. |
| 2011/0035221 A1 | 2/2011 | Zhang et al. |
| 2011/0063405 A1 | 3/2011 | Yam |
| 2011/0063429 A1 | 3/2011 | Contolini et al. |
| 2011/0066425 A1 | 3/2011 | Hudgins et al. |
| 2011/0071675 A1 | 3/2011 | Wells et al. |
| 2011/0096941 A1 | 4/2011 | Marzetta et al. |
| 2011/0119163 A1 | 5/2011 | Smith |
| 2011/0145013 A1 | 6/2011 | McLaughlin |
| 2011/0150420 A1 | 6/2011 | Cordonnier |
| 2011/0153520 A1 | 6/2011 | Coifman |
| 2011/0161113 A1 | 6/2011 | Rumak et al. |
| 2011/0166884 A1 | 7/2011 | Lesselroth |
| 2011/0178798 A1 | 7/2011 | Flaks et al. |
| 2011/0178813 A1 | 7/2011 | Moore |
| 2011/0202370 A1 | 8/2011 | Green, III et al. |
| 2011/0238435 A1 | 9/2011 | Rapaport |
| 2011/0246216 A1 | 10/2011 | Agrawal |
| 2011/0251852 A1 | 10/2011 | Blas |
| 2011/0286584 A1 | 11/2011 | Angel et al. |
| 2011/0301982 A1 | 12/2011 | Green, Jr. et al. |
| 2012/0020485 A1 | 1/2012 | Visser et al. |
| 2012/0029918 A1 | 2/2012 | Bachtiger |
| 2012/0053936 A1 | 3/2012 | Marvit |
| 2012/0076316 A1 | 3/2012 | Zhu et al. |
| 2012/0078626 A1 | 3/2012 | Tsai |
| 2012/0081504 A1 | 4/2012 | Ng |
| 2012/0101847 A1 | 4/2012 | Johnson et al. |
| 2012/0134507 A1 | 5/2012 | Dimitriadis et al. |
| 2012/0155703 A1 | 6/2012 | Hernandez-Abrego et al. |
| 2012/0158432 A1 | 6/2012 | Jain et al. |
| 2012/0159378 A1* | 6/2012 | Grassl .................. G16H 10/20 715/780 |
| 2012/0159391 A1 | 6/2012 | Berry et al. |
| 2012/0173281 A1 | 7/2012 | DiLeila et al. |
| 2012/0197660 A1 | 8/2012 | Prodanovich |
| 2012/0208166 A1 | 8/2012 | Ernst et al. |
| 2012/0212337 A1 | 8/2012 | Montyne et al. |
| 2012/0215551 A1 | 8/2012 | Flanagan et al. |
| 2012/0215557 A1 | 8/2012 | Flanagan et al. |
| 2012/0215559 A1 | 8/2012 | Flanagan et al. |
| 2012/0239430 A1 | 9/2012 | Corfield |
| 2012/0253801 A1 | 10/2012 | Santos Lang et al. |
| 2012/0253811 A1 | 10/2012 | Breslin et al. |
| 2012/0254917 A1 | 10/2012 | Burkitt et al. |
| 2012/0323574 A1 | 12/2012 | Wang et al. |
| 2012/0323575 A1 | 12/2012 | Gibbon et al. |
| 2012/0323589 A1 | 12/2012 | Udani |
| 2013/0017834 A1 | 1/2013 | Han et al. |
| 2013/0035961 A1 | 2/2013 | Yegnanarayanan |
| 2013/0041682 A1 | 2/2013 | Gottlieb et al. |
| 2013/0041685 A1 | 2/2013 | Yegnanarayanan |
| 2013/0064358 A1 | 3/2013 | Nusbaum |
| 2013/0073306 A1 | 3/2013 | Shlain et al. |
| 2013/0080879 A1 | 3/2013 | Darling |
| 2013/0103400 A1 | 4/2013 | Yegnanarayanan et al. |
| 2013/0138457 A1 | 5/2013 | Ragusa |
| 2013/0173287 A1 | 7/2013 | Cashman et al. |
| 2013/0188923 A1 | 7/2013 | Hartley et al. |
| 2013/0238312 A1 | 9/2013 | Waibel |
| 2013/0238329 A1 | 9/2013 | Casella dos Santos |
| 2013/0238330 A1 | 9/2013 | Casella dos Santos |
| 2013/0246098 A1 | 9/2013 | Habboush et al. |
| 2013/0246329 A1 | 9/2013 | Pasquero et al. |
| 2013/0297347 A1 | 11/2013 | Cardoza et al. |
| 2013/0297348 A1 | 11/2013 | Cardoza et al. |
| 2013/0301837 A1 | 11/2013 | Kim et al. |
| 2013/0311190 A1 | 11/2013 | Reiner |
| 2013/0325488 A1 | 12/2013 | Carter |
| 2013/0332004 A1 | 12/2013 | Gompert et al. |
| 2013/0339030 A1 | 12/2013 | Ehsani et al. |
| 2014/0019128 A1 | 1/2014 | Riskin et al. |
| 2014/0035920 A1 | 2/2014 | Duwenhorst |
| 2014/0050307 A1 | 2/2014 | Yuzefovich |
| 2014/0073880 A1 | 3/2014 | Boucher |
| 2014/0074454 A1 | 3/2014 | Brown |
| 2014/0093135 A1 | 4/2014 | Reid et al. |
| 2014/0096091 A1 | 4/2014 | Reid et al. |
| 2014/0122109 A1 | 5/2014 | Ghanbari et al. |
| 2014/0142944 A1 | 5/2014 | Ziv et al. |
| 2014/0164994 A1 | 6/2014 | Myslinski |
| 2014/0169767 A1 | 6/2014 | Goldberg |
| 2014/0188475 A1 | 7/2014 | Lev-Tov et al. |
| 2014/0207491 A1 | 7/2014 | Zimmerman et al. |
| 2014/0222526 A1 | 8/2014 | Shakil et al. |
| 2014/0223467 A1 | 8/2014 | Hayton et al. |
| 2014/0249818 A1 | 9/2014 | Yegnanarayanan et al. |
| 2014/0249830 A1 | 9/2014 | Gallopyn |
| 2014/0249831 A1 | 9/2014 | Gallopyn et al. |
| 2014/0249847 A1 | 9/2014 | Soon-Shlong et al. |
| 2014/0278522 A1 | 9/2014 | Ramsey et al. |
| 2014/0278536 A1 | 9/2014 | Zhang et al. |
| 2014/0279893 A1 | 9/2014 | Branton |
| 2014/0281974 A1 | 9/2014 | Shi et al. |
| 2014/0288968 A1 | 9/2014 | Johnson |
| 2014/0306880 A1 | 10/2014 | Greif et al. |
| 2014/0324477 A1 | 10/2014 | Oez |
| 2014/0330586 A1 | 11/2014 | Riskin et al. |
| 2014/0337016 A1 | 11/2014 | Herbig et al. |
| 2014/0337048 A1 | 11/2014 | Brown |
| 2014/0343939 A1 | 11/2014 | Mathias et al. |
| 2014/0358585 A1 | 12/2014 | Reiner |
| 2014/0362253 A1 | 12/2014 | Kim et al. |
| 2014/0365239 A1 | 12/2014 | Sadeghi |
| 2014/0365241 A1 | 12/2014 | Dillie et al. |
| 2014/0365242 A1 | 12/2014 | Neff |
| 2015/0046183 A1 | 2/2015 | Cireddu |
| 2015/0046189 A1 | 2/2015 | Dao |
| 2015/0052541 A1 | 2/2015 | Cheng |
| 2015/0070507 A1 | 3/2015 | Kagan |
| 2015/0086038 A1 | 3/2015 | Stein et al. |
| 2015/0088514 A1 | 3/2015 | Typrin |
| 2015/0088546 A1 | 3/2015 | Balram et al. |
| 2015/0120305 A1 | 4/2015 | Buck et al. |
| 2015/0120321 A1 | 4/2015 | David et al. |
| 2015/0124277 A1 | 5/2015 | Ono et al. |
| 2015/0124975 A1 | 5/2015 | Pontoppidan |
| 2015/0172262 A1 | 6/2015 | Ortiz, Jr. et al. |
| 2015/0172319 A1 | 6/2015 | Rodniansky |
| 2015/0182296 A1 | 7/2015 | Daon |
| 2015/0185312 A1 | 7/2015 | Gaubitch et al. |
| 2015/0187209 A1 | 7/2015 | Brandt |
| 2015/0248882 A1 | 9/2015 | Ganong, III et al. |
| 2015/0278449 A1 | 10/2015 | Laborde |
| 2015/0278534 A1 | 10/2015 | Thiyagarajan et al. |
| 2015/0290802 A1 | 10/2015 | Buehler et al. |
| 2015/0294079 A1 | 10/2015 | Bergougnan |
| 2015/0294089 A1 | 10/2015 | Nichols |
| 2015/0302156 A1 | 10/2015 | Parsadoust |
| 2015/0310174 A1 | 10/2015 | Coudert et al. |
| 2015/0310362 A1 | 10/2015 | Huffman |
| 2015/0356250 A1 | 12/2015 | Polimeni |
| 2015/0379200 A1 | 12/2015 | Gifford et al. |
| 2015/0379209 A1 | 12/2015 | Kusuma et al. |
| 2016/0012198 A1 | 1/2016 | Gainer, III et al. |
| 2016/0034643 A1 | 2/2016 | Zasowski et al. |

(56) References Cited

U.S. PATENT DOCUMENTS

| | | |
|---|---|---|
| 2016/0063206 A1 | 3/2016 | Wlson |
| 2016/0064000 A1 | 3/2016 | Mizumoto et al. |
| 2016/0098521 A1 | 4/2016 | Koziol |
| 2016/0119338 A1 | 4/2016 | Cheyer |
| 2016/0148077 A1 | 5/2016 | Cox et al. |
| 2016/0163331 A1 | 6/2016 | Yamaguchi |
| 2016/0165350 A1 | 6/2016 | Benattar |
| 2016/0174903 A1 | 6/2016 | Cutaia |
| 2016/0176375 A1 | 6/2016 | Bolton et al. |
| 2016/0179770 A1 | 6/2016 | Koll et al. |
| 2016/0188809 A1 | 6/2016 | Legorburn |
| 2016/0191357 A1 | 6/2016 | Orner et al. |
| 2016/0196821 A1 | 7/2016 | Yegnanarayanan et al. |
| 2016/0203327 A1 | 7/2016 | Akkiraju et al. |
| 2016/0217807 A1 | 7/2016 | Gainsboro |
| 2016/0232329 A1* | 8/2016 | Xu .................. G06F 40/186 |
| 2016/0234034 A1 | 8/2016 | Mahar et al. |
| 2016/0261930 A1 | 9/2016 | Kim |
| 2016/0275187 A1 | 9/2016 | Chowdhury et al. |
| 2016/0300020 A1 | 10/2016 | Wetta et al. |
| 2016/0342845 A1 | 11/2016 | Tien-Spalding et al. |
| 2016/0350950 A1 | 12/2016 | Ritchie et al. |
| 2016/0357538 A1 | 12/2016 | Lewallen et al. |
| 2016/0358632 A1 | 12/2016 | Lakhani et al. |
| 2016/0360336 A1 | 12/2016 | Gross et al. |
| 2016/0364606 A1 | 12/2016 | Conway et al. |
| 2017/0004260 A1 | 1/2017 | Moturu et al. |
| 2017/0011194 A1 | 1/2017 | Arshad et al. |
| 2017/0011740 A1 | 1/2017 | Gauci |
| 2017/0017834 A1 | 1/2017 | Sabitov et al. |
| 2017/0019744 A1 | 1/2017 | Matsumoto et al. |
| 2017/0046326 A1 | 2/2017 | Waibel |
| 2017/0069226 A1 | 3/2017 | Spinelli et al. |
| 2017/0076619 A1 | 3/2017 | Wallach et al. |
| 2017/0083214 A1 | 3/2017 | Furesjo et al. |
| 2017/0091246 A1 | 3/2017 | Risvik et al. |
| 2017/0093848 A1 | 3/2017 | Poisner et al. |
| 2017/0116384 A1 | 4/2017 | Ghani |
| 2017/0116392 A1 | 4/2017 | Casella dos Santos |
| 2017/0131384 A1 | 5/2017 | Davis et al. |
| 2017/0178664 A1 | 6/2017 | Wingate et al. |
| 2017/0197636 A1 | 7/2017 | Beauvais |
| 2017/0228500 A1 | 8/2017 | Massengale |
| 2017/0242840 A1 | 8/2017 | Lu et al. |
| 2017/0316775 A1 | 11/2017 | Le et al. |
| 2017/0334069 A1 | 11/2017 | Wang et al. |
| 2018/0004915 A1 | 1/2018 | Talbot et al. |
| 2018/0025093 A1 | 1/2018 | Xia et al. |
| 2018/0032702 A1 | 2/2018 | Casella dos Santos |
| 2018/0060282 A1 | 3/2018 | Kaljurand |
| 2018/0075845 A1 | 3/2018 | Kochura |
| 2018/0081859 A1 | 3/2018 | Snider et al. |
| 2018/0107815 A1 | 4/2018 | Wu et al. |
| 2018/0122506 A1 | 5/2018 | Grantcharov et al. |
| 2018/0130554 A1 | 5/2018 | Cheng |
| 2018/0144120 A1 | 5/2018 | Fram |
| 2018/0144747 A1 | 5/2018 | Skarbovsky et al. |
| 2018/0156887 A1 | 6/2018 | Qui et al. |
| 2018/0158461 A1 | 6/2018 | Wolff et al. |
| 2018/0158555 A1 | 6/2018 | Cashman et al. |
| 2018/0167243 A1 | 6/2018 | Gerdes |
| 2018/0181716 A1 | 6/2018 | Mander et al. |
| 2018/0197544 A1 | 7/2018 | Brooksby et al. |
| 2018/0197548 A1 | 7/2018 | Palakodety |
| 2018/0218731 A1 | 8/2018 | Gustafson |
| 2018/0225277 A1 | 8/2018 | Alba |
| 2018/0232591 A1 | 8/2018 | Hicks et al. |
| 2018/0240538 A1 | 8/2018 | Koll |
| 2018/0261307 A1 | 9/2018 | Couse et al. |
| 2018/0277017 A1 | 9/2018 | Cheung |
| 2018/0289291 A1 | 10/2018 | Richie |
| 2018/0310114 A1 | 10/2018 | Eronen et al. |
| 2018/0314689 A1 | 11/2018 | Wang et al. |
| 2018/0315428 A1 | 11/2018 | Johnson et al. |
| 2018/0336275 A1 | 11/2018 | Graham |
| 2019/0005959 A1 | 1/2019 | Cameron et al. |
| 2019/0012449 A1 | 1/2019 | Cheyer |
| 2019/0042606 A1 | 2/2019 | Griffith et al. |
| 2019/0051395 A1 | 2/2019 | Owen et al. |
| 2019/0096534 A1 | 3/2019 | Joao |
| 2019/0121532 A1 | 4/2019 | Strader et al. |
| 2019/0122766 A1 | 4/2019 | Strader et al. |
| 2019/0130073 A1 | 5/2019 | Sun et al. |
| 2019/0141031 A1 | 5/2019 | Devdas et al. |
| 2019/0172493 A1 | 6/2019 | Khan et al. |
| 2019/0182124 A1 | 6/2019 | Jeuk et al. |
| 2019/0214121 A1 | 7/2019 | O'Keeffe et al. |
| 2019/0246075 A1 | 8/2019 | Khadloya et al. |
| 2019/0251156 A1 | 8/2019 | Waibel |
| 2019/0265345 A1 | 8/2019 | Jungmaier et al. |
| 2019/0272844 A1 | 9/2019 | Sharma et al. |
| 2019/0313903 A1 | 10/2019 | McKinnon |
| 2019/0347269 A1* | 11/2019 | Xu .................. G16H 80/00 |
| 2020/0005939 A1 | 1/2020 | Stevens et al. |
| 2020/0005949 A1 | 1/2020 | Warkentine |
| 2020/0034753 A1 | 1/2020 | Hammad |
| 2020/0279107 A1 | 9/2020 | Staar et al. |
| 2021/0099433 A1 | 4/2021 | Soryal |

FOREIGN PATENT DOCUMENTS

| | | |
|---|---|---|
| EP | 1769771 A1 | 4/2007 |
| EP | 1927221 B1 | 11/2013 |
| JP | 2011182857 A | 9/2011 |
| JP | 2015533248 A | 11/2015 |
| KR | 20130118510 A | 10/2013 |
| WO | 0008585 A2 | 2/2000 |
| WO | 2013082087 A1 | 6/2013 |
| WO | 2014101472 A1 | 3/2014 |
| WO | 2014134089 A1 | 9/2014 |
| WO | 2016125053 A1 | 8/2016 |
| WO | 20160126813 A2 | 8/2016 |
| WO | 20160149794 A1 | 9/2016 |
| WO | 2017031972 A1 | 3/2017 |
| WO | 2017100334 A1 | 6/2017 |
| WO | 2017138934 A2 | 8/2017 |
| WO | 2018132336 A1 | 7/2018 |
| WO | 2019032778 A1 | 2/2019 |

OTHER PUBLICATIONS

Final Office Action issued in related U.S. Appl. No. 16/059,895, dated Jul. 6, 2020.
Non-Final Office Action issued in related U.S. Appl. No. 16/059,944, dated Jul. 13, 2020.
Notice of Allowance issued in related U.S. Appl. No. 16/271,616 dated Jul. 13, 2020.
Non-Final Office Action issued in related U.S. Appl. No. 16/058,826, dated Jul. 17, 2020.
Non-Final Office Action issued in related U.S. Appl. No. 16/058,914, dated Jul. 17, 2020.
Non-Final Office Action issued in related U.S. Appl. No. 16/058,925 dated Jul. 20, 2020.
Non-Final Office Action issued in related U.S. Appl. No. 16/058,894 dated Jul. 30, 2020.
Non-Final Office Action issued in related U.S. Appl. No. 16/292,877 dated Jul. 23, 2020.
Non-Final Office Action issued in related U.S. Appl. No. 16/058,883 dated Jul. 31, 2020.
Non-Final Office Action issued in related U.S. Appl. No. 16/058,829 dated Aug. 5, 2020.
Final Office Action issued in related U.S. Appl. No. 16/058,856 dated Aug. 12, 2020.
Final Office Action issued in related U.S. Appl. No. 16/292,920 dated Aug. 11, 2020.
Non-Final Office Action issued in related U.S. Appl. No. 16/058,912 dated Aug. 20, 2020.
Non-Final Office Action issued in related U.S. Appl. No. 16/100,030 dated Aug. 25, 2020.
Non-Final Office Action issued in related U.S. Appl. No. 16/059,818 dated Aug. 25, 2020.

(56) References Cited

OTHER PUBLICATIONS

Non-Final Office Action issued in related U.S. Appl. No. 16/058,803 dated Sep. 3, 2020.
Non-Final Office Action issued in related U.S. Appl. No. 16/271,029 dated Sep. 8, 2020.
Non-Final Office Action issued in related U.S. Appl. No. 16/293,032 dated Sep. 16, 2020.
Lenert, L. A. et al., "Design and Evaluation of a Wireless Electronic Health Records System for Field Care in Mass Casualty Settings", Journal of the American Medical Informatics Association, <https://www.ncbi.nlm.nih.gov/pmc/articles/PMC3198000, vol. 18, No. 6, (2011), pp. 842-852.
International Search Report issued in related PCT Application Serial No. PCT/US2019/020742 dated May 14, 2019.
International Search Report issued in related PCT Application Serial No. PCT/US2019/020739 dated May 17, 2019.
International Search Report issued in related PCT Application Serial No. PCT/US2019/020763 dated May 23, 2019.
International Search Report issued in related PCT Application Serial No. PCT/US2019/020765 dated May 23, 2019.
International Search Report issued in related PCT Application Serial No. PCT/US2019/020778 dated May 23, 2019.
International Search Report issued in related PCT Application Serial No. PCT/US2019/020771 dated May 30, 2019.
Non-Final Office Action issued in related U.S. Appl. No. 16/059,818 dated Jun. 10, 2019.
International Search Report issued in related PCT Application Serial No. PCT/US2019/020721 dated Jun. 6, 2019.
International Search Report issued in related PCT Application Serial No. PCT/US2019/020755 dated Jun. 6, 2019.
Final Office Action issued in related U.S. Appl. No. 16/059,967 dated Jul. 11, 2019.
Final Office Action issued in related U.S. Appl. No. 16/100,030 dated Jul. 18, 2019.
Non-Final Office Action issued in related U.S. Appl. No. 16/058,951 dated Jul. 25, 2019.
International Search Report issued in related International App. No. PCT/US2019/020788 dated Jul. 17, 2019.
Final Office Action issued in related U.S. Appl. No. 16/058,912 dated Jul. 31, 2019.
Final Office Action issued in related U.S. Appl. No. 16/059,944 dated Aug. 22, 2019.
Non-Final Office Action issued in related U.S. Appl. No. 16/058,871 dated Sep. 23, 2019.
Final Office Action issued in related U.S. Appl. No. 16/059,818 dated Sep. 25, 2019.
Notice of Allowance issued in related U.S. Appl. No. 16/100,030 dated Oct. 9, 2019.
Non-Final Office Action issued in related U.S. Appl. No. 16/192,427 dated Oct. 3, 2019.
Non-Final Office Action issued in related U.S. Appl. No. 16/271,616 dated Nov. 15, 2019.
Non-Final Office Action issued in related U.S. Appl. No. 16/192,358 dated Nov. 19, 2019.
Non-Final Office Action issued in related U.S. Appl. No. 16/059,944 dated Dec. 23, 2019.
Non-Final Office Action issued in related U.S. Appl. No. 16/059,818 dated Jan. 9, 2020.
Non-Final Office Action issued in related U.S. Appl. No. 16/058,912 dated Jan. 27, 2020.
Non-Final Office Action issued in related U.S. Appl. No. 16/292,920 dated Feb. 28, 2020.
Non-Final Office Action issued in related U.S. Appl. No. 16/100,030, dated Mar. 4, 2020.
Notice of Allowance issued in related U.S. Appl. No. 16/271,616, dated Mar. 17, 2019.
Dibiase, J. H. et al., "Robust Localization in Reverberant Rooms," in Microphone Arrays—Signal Processing Techniques and Applications, Ch. 8, pp. 157-180.

Valin, Jean-Marc et al., "Robust Sound Source Localization Using a Microphone Array on a Mobile Robot," Proceedings of the 2003 IEEE/RSJ International Conference on Intelligent Robots and Systems, vol. 2, 2003, pp. 1228-1233.
Wang, L. et al., "Over-determined Source Separation and Localization Using Distributed Microphone," IEEE/ACM Transactions on Audio, Speech, and Language Processing, vol. 24, No. 9, Sep. 2016, pp. 1573-1588.
Notice of Allowance issued in related U.S. Appl. No. 16/108,959, dated Nov. 6, 2019.
Bahdanau, D. et al., "Neural Machine Translation by Jointly Learning to Align and Translate", Published as a Conference Paper at ICLR 2015, May 19, 2016, 15 pages.
Final Office Action issued in related U.S. Appl. No. 16/192,427, dated Mar. 6, 2020.
Final Office Action issued in related U.S. Appl. No. 16/058,871, dated Mar. 19, 2020.
Final Office Action issued in related U.S. Appl. No. 16/059,944, dated Mar. 26, 2020.
Non-Final Office Action issued in related U.S. Appl. No. 16/058,936, dated Apr. 15, 2020.
Non-Final Office Action issued in related U.S. Appl. No. 16/058,941, dated Apr. 15, 2020.
Non-Final Office Action issued in related U.S. Appl. No. 16/059,895, dated Apr. 24, 2020.
Non-Final Office Action issued in related U.S. Appl. No. 16/059,974, dated Apr. 24, 2020.
Non-Final Office Action issued in related U.S. Appl. No. 16/059,986, dated Apr. 24, 2020.
Final Office Action issued in related U.S. Appl. No. 16/100,310, dated May 8, 2020.
Final Office Action issued in related U.S. Appl. No. 16/058,912, dated May 26, 2020.
Non-Final Office Action issued in related U.S. Appl. No. 16/271,616, dated May 29, 2020.
Final Office Action issued in related U.S. Appl. No. 16/192,358, dated Jun. 2, 2020.
Non-Final Office Action issued in related U.S. Appl. No. 16/292,895, dated Jun. 5, 2020.
Final Office Action issued in related U.S. Appl. No. 16/058,941, dated Jun. 23, 2020.
Final Office Action issued in U.S. Appl. No. 16/058,936, dated Jun. 23, 2020.
Non-Final Office Action issued in related U.S. Appl. No. 16/058,856 dated Jul. 2, 2020.
Final Office Action issued in related U.S. Appl. No. 16/059,986, dated Jul. 6, 2020.
Non-Final Office Action issued in related U.S. Appl. No. 16/059,944 dated Sep. 28, 2018.
International Search Report and Written Opinion dated Oct. 2, 2018 in related International Application Serial No. PCT/US2018/045923.
International Search Report and Written Opinion dated Oct. 3, 2018 in related International Application Serial No. PCT/US2018/046024.
International Search Report and Written Opinion dated Oct. 3, 2018 in related International Application Serial No. PCT/US2018/045982.
International Search Report and Written Opinion dated Oct. 3, 2018 in related International Application Serial No. PCT/US2018/046008.
International Search Report and Written Opinion dated Oct. 2, 2018 in related International Application Serial No. PCT/US2018/046034.
International Search Report and Written Opinion dated Oct. 3, 2018 in related International Application Serial No. PC/US2018/045926.
International Search Report and Written Opinion dated Sep. 21, 2018 in related International Application Serial No. PCT/US2018/046002.
Non-Final Office Action issued in related U.S. Appl. No. 16/059,818 dated Nov. 2, 2018.

(56) References Cited

OTHER PUBLICATIONS

International Search Report and Written Opinion dated Oct. 24, 2018 in related International Application Serial No. PCT/US2018/046041.
International Search Report and Written Opinion dated Oct. 16, 2018 in related International Application Serial No. PCT/US2018/046029.
International Search Report and Written Opinion dated Oct. 11, 2018 in related International Application Serial No. PCT/US2018/045994.
International Search Report and Written Opinion dated Oct. 22, 2018 in related International Application Serial No. PCT/US2018/045903.
International Search Report and Written Opinion dated Oct. 22, 2018 in related International Application Serial No. PCT/US2018/045917.
Klann, J. et el., "An Intelligent Listening Framework for Capturing Encounter Notes from a Doctor-Patient Dialog", BMC Med Inform Decis Mak. 2009; 9(Suppl 1): S3, Published online Nov. 3, 2009. doi: 10.1186/1472-6947-9-S1-S3, 5 pages.
Non-Final Office Action issued in related U.S. Appl. No. 16/058,871 dated Dec. 3, 2018.
International Search Report dated Oct. 30, 2018 in related International Application Serial No. PCT/US2018/045971.
International Search Report issued in PCT Application Serial No. PCT/US2018/046049 dated Nov. 2, 2018.
International Search Report issued in PCT Application Serial No. PCT/US2018/045921 dated Oct. 16, 2018.
International Search Report issued in PCT Application Serial No. PCT/US2018/045896 dated Oct. 17, 2018.
Non-Final Office Action issued in related U.S. Appl. No. 16/059,967 dated Jan. 2, 2019.
Non-Final Office Action issued in related U.S. Appl. No. 16/058,951 dated Oct. 5, 2018.
Kale, G. V. et al., "A Study of Vision based Human Motion Recognition and Analysis", International Journal of Ambient Computing and Intelligence, vol. 7, Issue 2, Jul.-Dec. 2016, 18 pages.
International Search Report issued in PCT Application Serial No. PCT/US2018/045908 dated Oct. 19, 2018.
International Search Report issued in PCT Application Serial No. PCT/US2018/045936 dated Oct. 18, 2018.
International Search Report issued in PCT Application Serial No. PCT/US2018/045987 dated Oct. 12, 2018.
International Search Report issued in PCT Application Serial No. PCT/US2018/046006 dated Oct. 15, 2018.
Invitation to Pay Additional Fees and, Where Applicable, Protest Fee issued In PCT Application Serial No. PCT/US2012/072041 dated Jun. 6, 2013.
International Search Report issued in related PCT Application Serial No. PCT/US2012/072041 dated Aug. 2, 2013.
Alapetite, A. et al., "Introducing vocal modality into electronics anaesthesia record systems: possible effects on work practices in the operating room", EACE '05 Proceedings of the 2005 Annual Conference on European Association of Cognitive Ergonomics, (2005), pp. 197-204.
Alapetite, A., "Speech recognition for the anaesthesia record during crisis scenarios", International Journal of Medical Informatics, 2008, vol. 77, No. 1, pp. 448-460.
Cimiano, P. et al., "Learning Concept Hierarchies from Text with a Guided Hierarchical Clustering algorithm", in C. Biemann and G. Paas (eds.), Proceedings of the ICML 2005 Workshop on Learning and Extending Lexical Ontologies with Machine Learning Methods, Bonn, Germany, 2005, 10 pages.
Fan, J. et al., "Prismatic: Inducing Knowledge from a Large Scale Lexicalized Relation Resource", Proceedings of the NAACL HLT 2010 First International Workshop on Formalisms and Methodology for Learning by Reading, Los Angeles, California, Jun. 2010, pp. 122-127.
Florian, R. et al., "A Statistical Model for Multilingual Entity Detection and Tracking", Proceedings of the Human Language Technologies Conference, (2004), 8 pages.
Gomez-Perez, A. et al., "An overview of methods and tools for ontology learning from texts", Knowledge Engineering Review, vol. 19, No. 3, (Sep. 2004), pp. 187-212.
Grasso, M. A., "Automated Speech Recognition in Medical Applications", M. D. Computing, vol. 12, No. (1995), 8 pages.
Harris, M. D., "Building a Large-scale Commercial NLG System for an EMR", Proceedings of the Fifth International Natural Language Generation Conference, (2008), pp. 157-160.
Jungk, A. et al., "A Case Study in Designing Speech Interaction with a Patient Monitor", Journal of Clinical Monitoring and Computing, vol. 16, (2000), pp. 295-307.
Klann, J. G. et al., "An intelligent listening framework for capturing encounter notes from a doctor-patient dialog", BMC Medical Informatics and Decision Making, vol. 9, (2009), published Nov. 3, 2009, 10 pages.
Meng, F. et al., Generating Models of Surgical Procedures using UMLS Concepts and Multiple Sequence Alignment, AMIA Annual Symposium Proceedings, (2005), pp. 520-524.
Szolovits, P. et al., "FairWtness: Capturing Patient-Provider Encounter through Text, Speech, and Dialogue Processing", MIT Computer Science and Artificial Intelligence Laboratory (CSAIL) Clinical Decision Making Group. Last updated on Apr. 9, 2010, http://groups.csail.mit.edu/medg/projects/fw/, 3 pages.
Welty, C. et al., "Large Scale Relation Detection", Proceedings of the NAACL HLT 2010 First International Workshop on Formalisms and Methodology for Learning by Reading, Association of Computational Linguistics, Los Angeles, CA, Jun. 2010, pp. 24-33.
Zafar, A. et al., "Continuous Speech Recognition for Clinicians", Technology Evaluation, Journal of the American Medical Informatics Association, vol. 6, No. 3, May/Jun. 1999, pp. 195-204.
Final Office Action issued in related U.S. Appl. No. 16/059,818 dated Feb. 28, 2019.
Non-Final Office Action issued in related U.S. Appl. No. 16/100,030 dated Feb. 28, 2019.
Non-Final Office Action issued in related U.S. Appl. No. 16/058,912 dated Mar. 6, 2019.
Final Office Action issued in related U.S. Appl. No. 16/058,951 dated Apr. 4, 2019.
Final Office Action issued in related U.S. Appl. No. 16/058,871 dated Apr. 8, 2019.
Non-Final Office Action issued in related U.S. Appl. No. 16/059,944 dated Apr. 15, 2019.
International Search Report issued in related PCT Application Serial No. PCT/US2019/020746 dated May 14, 2019.
Non-Final Office Action issued in related U.S. Appl. No. 16/292,920 dated Mar. 26, 2021.
Non-Final Office Action issued in related U.S. Appl. No. 16/270,888 dated Mar. 26, 2021.
Non-Final Office Action issued in related U.S. Appl. No. 16/271,329 dated Mar. 26, 2021.
Hu et al., "Deep Multimodel Speaker Naming", Computing Research Repository, vol. abs/1507.04831, 2015 (Year: 2015).
Final Office Action issued in related U.S. Appl. No. 16/271,029 dated Apr. 1, 2021.
Non-Final Office Action issued in related U.S. Appl. No. 16/058,826 dated Apr. 6, 2021.
Notice of Allowance issued in related U.S. Appl. No. 16/058,871 dated Apr. 9, 2021.
Final Office Action issued in related U.S. Appl. No. 17/084,310 dated Apr. 12, 2021.
Non-Final Office Action issued in related U.S. Appl. No. 16/441,740 dated Apr. 14, 2021.
Non-Final Office Action issued in related U.S. Appl. No. 16/442,247 dated Apr. 15, 2021.
Non-Final Office Action issued in related U.S. Appl. No. 16/058,925 dated Apr. 16, 2021.
Non-Final Office Action issued in related U.S. Appl. No. 16/058,914 dated Apr. 16, 2021.
Non-Final Office Action issued in related U.S. Appl. No. 16/058,894 dated Apr. 16, 2021.

(56) References Cited

OTHER PUBLICATIONS

Supplementary European Search Report issued in counterpart Application Serial No. 188344752.8 dated Mar. 3, 2021.
Non-Final Office Action issued in related U.S. Appl. No. 16/058,883 dated Apr. 28, 2021.
Notice of Allowance issued in related U.S. Appl. No. 16/059,944 dated Apr. 30, 2021.
Final Office Action issued in related U.S. Appl. No. 16/270,782 dated May 7, 2021.
Notice of Allowance issued in related U.S. Appl. No. 16/441,777 dated May 14, 2021.
Final Office Action issued in related U.S. Appl. No. 17/084,448 dated Jun. 1, 2021.
Non-Final Office Action issued in related U.S. Appl. No. 16/292,893 dated Jun. 9, 2021.
Notice of Allowance issued in related U.S. Appl. No. 16/058,871 dated Jun. 14, 2021.
Non-Final Office Action issued in related U.S. Appl. No. 16/293,032 dated Jun. 24, 2021.
Non-Final Office Action issued in related U.S. Appl. No. 16/058,803 dated Jun. 24, 2021.
Non-Final Office Action issued in related U.S. Appl. No. 16/058,829 dated Jun. 25, 2021.
Final Office Action issued in related U.S. Appl. No. 16/192,358 dated Jun. 25, 2021.
Notice of Allowance issued in related U.S. Appl. No. 16/059,818 dated Jul. 2, 2021.
Notice of Allowance issued in related U.S. Appl. No. 16/058,936 dated Jul. 7, 2021.
Notice of Allowance issued in related U.S. Appl. No. 17/084,310 dated Jul. 9, 2021.
Notice of Allowance issued in related U.S. Appl. No. 16/058,941 dated Jul. 14, 2021.
Notice of Allowance issued in related U.S. Appl. No. 16/292,920 dated Jul. 15, 2021.
Non-Final Office Action issued in related U.S. Appl. No. 16/773,447 dated Jul. 20, 2021.
Notice of Allowance issued in related U.S. Appl. No. 16/442,247 dated Jul. 22, 2021.
Communication issuing supplementary European Search Report dated May 14, 2021 and Extended European Search Report dated Apr. 16, 2021 in counterpart Application Serial No. EP 18844226.3.
Communication issuing supplementary European Search Report dated Apr. 8, 2021 and Extended European Search Report dated Mar. 10, 2021 in counterpart Application Serial No. EP 18845046.4.
YouTube video clip entitled "Nuance PowerMic Mobile gives clinicians greater mobility", retrieved from Internet: https://www.youtube.com/watch?v=OjqiePRFtl@feature=emb-logo (Year: 2015), 3 pages.
Gross R, et al: "Towards a multimodal meeting record", Multimedia and Expo, 2000. ICME 2000. 2000 IEEE International Conference in New York, NY, USA Jul. 30-Aug. 2, 2000, Piscataway, NJ, USA, IEEE, US, vol. 3, Jul. 30, 2000 (Jul. 30, 2000_, pp. 1593-1596, XP010512812, DOI: 10.1109/ICME.2000.871074 ISBN: 978-0-7803-6536-0 *the whole document*.
Communication issuing supplementary European Search Report dated Apr. 8, 2021 and Extended European Search Report dated Mar. 10, 2021 counterpart Application Serial No. EP 18842996.3.
Communication issuing supplementary European Search Report dated May 19, 2021 and Extended European Search Report dated Apr. 19, 2021 in counterpart Application Serial No. EP 18844530.8.
Communication issuing supplementary European Search Report dated May 19, 2021 and Extended Europe Search Report dated Apr. 19, 2021 in counterpart Application Serial No. EP 18843844.1.
Nadir, Weibel, et al.: "Lab-in-a-Box: semi-automatic tracking of activity in the medical office", Personal and Ubiqitous Computing, Springer Verlag, Lond, GB, vol. 19, No. 2, Sep. 28, 2014 (Sep. 28, 2014); pp. 317-334, XP058066121, ISSN: 1617-4909, DOI: 10.1007/

S00779-014-0821-0 *abstract* *Section 4, The Lab-in-a-Box; p. 321-p. 327* *Section 5.2, "Data collection and analysis"; p. 330-p. 331* *table 1* *figures 7,8*.
Communication issuing supplementary European Search Report dated May 28, 2021 and Extended European Search Report dated May 3, 2021 in counterpart Application Serial No. EP 18843648.9.
Communication issuing supplementary European Search Report dated May 28, 2021 and Extended European Search Report dated Apr. 16, 2021 in counterpart Application Serial No. EP 18843945.9.
Yang, et al., "The Design and Implementation of a Smart e-Receptionist", IEE Potentials, IEEE, New York, NY, US, vo. 32, No. 4, Jul. 22, 2013 (Jul. 22, 2013), pp. 22-27, XP011522905, ISSN: 0278-6648, DOI: 10.1109/MPOT.2012.2213851 *the whole document*.
Communication issuing supplementary European Search Report dated May 14, 2021 and Extended European Search Report dated Apr. 16, 2021 in counterpart Application Serial No. EP 18843175.3.
Communication issuing supplementary European Search Report dated May 28, 2021 and Extended European Search Report dated Apr. 29, 2021 in counterpart Application Serial No. EP 18845144.7.
Non-Final Office Action dated Aug. 6, 2021 in counterpart U.S. Appl. No. 16/270,782.
Final Office Action dated Aug. 19, 2021 in counterpart U.S. Appl. No. 16/292,973.
Communication issuing supplementary European Search Report dated Apr. 12, 2021 and Extended European Search Report dated Mar. 12, 2021 in counterpart Application Serial No. EP 18843255.3.
Communication issuing supplementary European Search Report dated May 26, 2021 and Extended European Search Report dated Apr. 30, 2021 in counterpart Application Serial No. EP 18844675.1.
Non-Final Office Action issued in related U.S. Appl. No. 16/192,427 dated Sep. 21, 2020.
Non-Final Office Action issued in related U.S. Appl. No. 16/292,893 dated Oct. 2, 2020.
David, G. C. et al., "Listening to what is said-transcribing what is heard: the impact of speech recognition technology (SRT) on the practice of medical transcription (MT)", Sociology of Heath and Illness, vol. 31, No. 6, pp. 924-938, (2009).
Non-Final Office Action issued in related U.S. Appl. No. 16/058,871 dated Oct. 5, 2020.
Non-Final Office Action issued in related U.S. Appl. No. 16/058,941 dated Oct. 26, 2020.
Non-Final Office Action issued in related U.S. Appl. No. 16/058,936 dated Oct. 26, 2020.
International Search Report and Written Opinion dated Aug. 19, 2020 in PCT Application Serial No. PCT/US2020/037284.
Final Office Action issued in related U.S. Appl. No. 16/058,826, dated Nov. 30, 2020.
Final Office Action issued in related U.S. Appl. No. 16/058,803 dated Nov. 30, 2020.
Final Office Action issued in related U.S. Appl. No. 16/058,883 dated Nov. 30, 2020.
Final Office Action issued in related U.S. Appl. No. 16/058,925 dated Nov. 30, 2020.
Final Office Action issued in related U.S. Appl. No. 16/058,914, dated Nov. 30, 2020.
Final Office Action issued in related U.S. Appl. No. 16/292,895, dated Nov. 30, 2020.
Non-Final Office Action issued in related U.S. Appl. No. 16/192,358, dated Nov. 27, 2020.
Final Office Action issued in related U.S. Appl. No. 16/059,818 dated Dec. 4, 2020.
Non-Final Office Action issued in related U.S. Appl. No. 16/059,895, dated Dec. 9, 2020.
Final Office Action issued in related U.S. Appl. No. 17/084,310 dated Dec. 22, 2020.
Non-Final Office Action issued in related U.S. Appl. No. 16/059,974, dated Dec. 18, 2020.
Non-Final Office Action issued in related U.S. Appl. No. 16/059,986, dated Dec. 18, 2020.
International Search Report and Written Opinion dated Aug. 31, 2020 in PCT Application Serial No. PCT/US2020/037226.

(56) References Cited

OTHER PUBLICATIONS

Final Office Action issued in related U.S. Appl. No. 16/058,829 dated Jan. 11, 2021.
Non-Final Office Action issued in related U.S. Appl. No. 17/084,310, dated Dec. 21, 2020.
Notice of Allowance issued in related U.S. Appl. No. 16/100,030 dated Jan. 11, 2021.
Angles, R., "A Comparison of Current Graph Database Models", In: 2012 IEEE 28th International Conference on Data Engineering Workshops, Apr. 5, 2012 (Apr. 5, 2012) Retrieved on Aug. 5, 2020 (Aug. 5, 2020) from URL:https://ieeexplore.ieee.org/document/6313676 entire document, 7 pages.
Final Office Action issued in related U.S. Appl. No. 16/059,944 dated Dec. 28, 2020.
Final Office Action issued in related U.S. Appl. No. 16/058,894 dated Dec. 1, 2020.
Final Office Action issued in related U.S. Appl. No. 16/058,941 dated Dec. 22, 2020.
Notice of Allowance issued in related U.S. Appl. No. 16/058,856 dated Jan. 19, 2021.
Non-Final Office Action issued in related U.S. Appl. No. 16/270,782 dated Jan. 19, 2021.
Notice of Allowance issued in related U.S. Appl. No. 16/058,912 dated Jan. 22, 2021.
Final Office Action issued in related U.S. Appl. No. 16/292,893 dated Jan. 28, 2021.
Notice of Allowance issued in related U.S. Appl. No. 16/100,030 dated Jan. 28, 2021.
Non-Final Office Action issued in related U.S. Appl. No. 16/441,777 dated Feb. 4, 2021.
Final Office Action issued in related U.S. Appl. No. 16/292,877 dated Feb. 8, 2021.
Non-Final Office Action issued in related U.S. Appl. No. 17/084,448 dated Feb. 10, 2021.
Non-Final Office Action issued in related U.S. Appl. No. 16/292,973 dated Feb. 12, 2021.
Final Office Action issued in related U.S. Appl. No. 16/192,427 dated Feb. 22, 2021.
International Search Report and Written Opinion dated Jan. 11, 2021 in PCT Application Serial No. PCT/US2020/053504.
International Search Report and Written Opinion dated Nov. 15, 2019 in PCT Application Serial No. PCT/US2019/047689.
Final Office Action issued in related U.S. Appl. No. 16/293,032 dated Mar. 1, 2021.
Non-Final Office Action issued in related U.S. Appl. No. 16/270,888 dated Mar. 2, 2021.
Notice of Allowance issued in related U.S. Appl. No. 16/058,856 dated Mar. 9, 2021.
Final Office Action issued in related U.S. Appl. No. 16/058,871, dated Mar. 18, 2021.
Non-Final Office Action issued in related U.S. Appl. No. 16/059,818 dated Mar. 18, 2021.
Zhou et al., "Applying the Narve Bayes Classifier to Assist Users in Detecting Speech Recognition Errors," Proceedings of the 38th Annual Hawaii International Conference on System Sciences, Big Island, HI, USA, 2005, pp. 183b-183b, doi: 10.1109/HICSS.2005.99.
Abdulkader et al., "Low Cost Correction of OCR Errors Using Learning in a Multi-Engine Environment," 2009 10th International Conference on Document Analysis and Recognition, Barcelona, 2009, pp. 576-580, doi: 10.1109/ICDAR.2009.242.
Final Office Action issued in related U.S. Appl. No. 16/059,895 dated Mar. 24, 2021.
Final Office Action issued in related U.S. Appl. No. 16/059,974 dated Mar. 24, 2021.
Final Office Action issued in related U.S. Appl. No. 16/059,986 dated Mar. 24, 2021.
Non-Final Office Action issued in related U.S. Appl. No. 16/292,895 dated Mar. 25, 2021.

Communication issuing supplementary European Search Report dated Mar. 30, 2021 and Extended European Search Report dated Mar. 3, 2021 in counterpart Application Serial No. EP 18844752.8.
Shivappa, S. et al., "Role of Head Pse Estimation in Speech Acquisition from Distant Microphones," Acoustics, Speech and Signal Processing, ICASSP 2009, IEEE International Conference on IEEE, pp. 3557-3560, Apr. 19, 2009.
Communication issuing supplementary European Search Report dated Apr. 6, 2021 and Extended European Search Report dated Mar. 8, 2021 in counterpart Application Serial No. EP 18844407.9.
Communication issuing supplementary European Search Report dated Apr. 12, 2021 and Extended European Search Report dated Apr. 19, 2021 in counterpart Application Serial No. EP 18843873.3.
Communication issuing supplementary European Search Report dated Apr. 12, 2021 and Extended European Search Report dated Mar. 11, 2021 in counterpart Application Serial No. EP 18843329.6.
Communication issuing supplementary European Search Report dated Apr. 13, 2021 and Extended European Search Report dated Apr. 19, 2021 in counterpart Application Serial No. EP 18843586.1.
Communication issuing supplementary European Search Report dated Apr. 16, 2021 and Extended European Search Report dated Mar. 22, 2021 in counterpart Application Serial No. EP 18843254.6.
Communication issuing supplementary European Search Report dated May 26, 2021 and Extended European Search Report dated Apr. 30, 2021 in counterpart Application Serial No. EP 18844406.1.
Non-Final Office Action issued in counterpart U.S. Appl. No. 16/271,029 dated Sep. 15, 2021.
Notice of Allowance issued in counterpart U.S. Appl. No. 16/059,895 dated Sep. 13, 2021.
Final Office Action issued in counterpart U.S. Appl. No. 16/270,888 dated Sep. 9, 2021.
Notice of Allowance issued in counterpart U.S. Appl. No. 17/084,448 dated Sep. 22, 2021.
Non-Final Office Action issued in counterpart U.S. Appl. No. 16/059,967 dated Sep. 20, 2021.
Klaan et al., "An Intelligent listening framework for capturing encounter notes from a doctor-patient dialog," BMC Medical Informatics and Decision Making, vol. 9, Suppl, Suppl 1, S3. Nov. 2009.
Final Office Action issued in counterpart U.S. Appl. No. 16/292,895 dated Sep. 30, 2021.
Notice of Allowance issued in counterpart U.S. Appl. No. 16/059,974 dated Oct. 5, 2021.
Notice of Allowance issued in counterpart U.S. Appl. No. 16/059,986 dated Oct. 12, 2021.
Final Office Action issued in counterpart U.S. Appl. No. 16/058,826 dated Oct. 21, 2021.
Final Office Action issued in counterpart U.S. Appl. No. 16/058,894 dated Oct. 29, 2021.
Final Office Action issued in counterpart U.S. Appl. No. 16/058,883 dated Oct. 29, 2021.
Final Office Action issued in counterpart U.S. Appl. No. 16/058,925 dated Oct. 29, 2021.
Final Office Action issued in counterpart U.S. Appl. No. 16/058,914 dated Oct. 29, 2021.
Unknown, You Tube video clip entitled "Nuance Healthcare Florence Workflow Concept with Samsung Smartwatch Demo English," retrieved from Internet: https://www.youtube.com/watch?v=I-NVD60oyn) (Year: 2015).
Final Office Action issued in counterpart U.S. Appl. No. 16/292,893 dated Nov. 15, 2021.
Notice of Allowance issued counterpart U.S. Appl. No. 16/292,920 dated Nov. 10, 2021.
Notice of Allowance issued in counterpart U.S. Appl. No. 17/084,310 dated Nov. 12, 2021.
Notice of Allowance issued in counterpart U.S. Appl. No. 16/442,247 dated Nov. 15, 2021.
Notice of Allowance issued in counterpart U.S. Appl. No. 16/441,740 dated Nov. 15, 2021.
Luck, J. et al., Using standardized patients to measure physicians' practice: validation study using audio recordings. Bmj, 325(7366), 679 (2002).
Final Office Action issued in related U.S. Appl. No. 16/293,032 dated Nov. 19, 2021.

(56) References Cited

OTHER PUBLICATIONS

Non-Final Office Action issued in related U.S. Appl. No. 17/210,052 dated Nov. 19, 2021.
Notice of Allowance issued in related U.S. Appl. No. 16/192,427 dated Dec. 3, 2021.
International Search Report and Written Opinion dated Dec. 1, 2021 in PCT Application Serial No. PCT/US2021/056265.
Notice of Allowance issued in U.S. Appl. No. 16/192,427 dated Dec. 8, 2021.
Notice of Allowance issued in U.S. Appl. No. 16/271,329 dated Dec. 13, 2021.
Notice of Allowance issued in U.S. Appl. No. 16/773,447 dated Dec. 15, 2021.
Notice of Allowance issued in U.S. Appl. No. 16/059,986 dated Dec. 15, 2021.
Notice of Allowance issued in U.S. Appl. No. 16/270,782 dated Dec. 16, 2021.
Non-Final Office Action issued in U.S. Appl. No. 16/588,475 dated Jan. 10, 2022.
Notice of Allowance issued in U.S. Appl. No. 16/059,895 dated Jan. 18, 2022.
Non-Final Office Action issued in U.S. Appl. No. 16/270,888 dated Jan. 20, 2022.
Final Office Action issued in U.S. Appl. No. 16/271,029 dated Jan. 31, 2022.
Notice of Allowance issued in U.S. Appl. No. 17/084,448 dated Jan. 26, 2022.
Notice of Allowance issued in U.S. Appl. No. 17/210,052 dated Feb. 18, 2022.
Notice of Allowance issued in U.S. Appl. No. 17/210,120 dated Mar. 1, 2022.
Notice of Allowance issued in U.S. Appl. No. 16/059,974 dated Feb. 4, 2022.
International Search Report issued in International Application No. PCT/US2021/056274 dated Dec. 7, 2021.
Notice of Allowance issued in U.S. Appl. No. 16/058,883 dated Mar. 25, 2022.
Non-Final Office Action issued in U.S. Appl. No. 16/058,826 dated Mar. 29, 2022.
Notice of Allowance issued in U.S. Appl. No. 16/058,914 dated Mar. 30, 2022.
Non-Final Office Action issued in U.S. Appl. No. 16/058,925 dated Mar. 30, 2022.
Van Hoff et al., Ageing-in-Place with the use of Ambient Intelligence Technology: Perspectives of Older Users, International Journal of Medical Informatics, vol. 80, Issue 5, May 2011, pp. 310-331.
Non-Final Office Action issued in U.S. Appl. No. 16/058,9894 dated Mar. 31, 2022.
Non-Final Office Action issued in U.S. Appl. No. 16/292,893 dated Mar. 29, 2022.
Final Office Action issued in U.S. Appl. No. 16/059,967 dated Apr. 1, 2022.
Non-Final Office Action issued in U.S. Appl. No. 16/292,973 dated Apr. 1, 2022.
Non-Final Office Action issued in U.S. Appl. No. 16/293,032 dated Apr. 5, 2022.
Non-Final Office Action issued in U.S. Appl. No. 16/292,877 dated Apr. 28, 2022.
Non-Final Office Action issued in U.S. Appl. No. 16/292,877 dated May 2, 2022.
Non-Final Office Action issued in U.S. Appl. No. 16/292,895 dated May 17, 2022.
Final Office Action issued in U.S. Appl. No. 16/058,803 dated May 18, 2022.
Non-Final Office Action issued in U.S. Appl. No. 16/058,914 dated May 24, 2022.
Notice of Allowance issued in U.S. Appl. No. 16/058,829 dated Jun. 9, 2022.
Non-Final Office Action issued in U.S. Appl. No. 16/271,029 dated Jun. 21, 2022.

* cited by examiner

SYSTEM AND METHOD FOR CUSTOMIZED TEXT MACROS

RELATED APPLICATION

This application claims the benefit of U.S. Provisional Application No. 62/868,474 filed on 28 Jun. 2019, the contents of which are all incorporated herein by reference.

BACKGROUND

Automated Clinical Documentation (ACD) may be used, e.g., to turn conversational (e.g., physician, patient, and/or other participants such as patient's family members, nurses, physician assistants, etc.) speech into formatted (e.g., medical) reports, potentially transcribing the speech as an intermediate step. Such reports may be reviewed, e.g., to assure accuracy of the reports by the physician, scribe, etc.

Summary of Disclosure

In one example implementation, a method, performed by one or more computing devices, may include but is not limited to encoding, by a computing device, a transcript and text macros into vector representations. A word by word report may be predicted based upon, at least in part, the encoding. An attention mechanism may be queried based upon, at least in part, a decoder state. An attention distribution may be produced over an encoder output. An interpolation of the encoder output may be produced based upon, at least in part, the attention distribution. The interpolation of the encoder output may be input into a decoder for report modeling that may include text macro location and content.

One or more of the following example features may be included. A decoder output may be augmented with a sentinel token, wherein the sentinel token may indicate the text macro is to be inserted at the location in the report. A probability for the text macro to be inserted at the location in the report may be produced based upon, at least in part, the transcript, the text macro, and preceding words in the report. The probability for the text macro to be inserted at the location in the report may be further based upon, at least in part, an encoded representation of an input to the encoder, and an encoded representation of the text macro. The text macro for the report may be displayed differently from non-text macro. Attributes of the text macro for the report may be displayed differently from non-text macro. Any of the text macros may be deleted from the report using a shortcut without requiring individual deletion of each character in content of the text macros.

In another example implementation, a computing system may include one or more processors and one or more memories configured to perform operations that may include but are not limited to encoding a transcript and text macros into vector representations. A word by word report may be predicted based upon, at least in part, the encoding. An attention mechanism may be queried based upon, at least in part, a decoder state. An attention distribution may be produced over an encoder output. An interpolation of the encoder output may be produced based upon, at least in part, the attention distribution. The interpolation of the encoder output may be input into a decoder for report modeling that may include text macro location and content.

One or more of the following example features may be included. A decoder output may be augmented with a sentinel token, wherein the sentinel token may indicate the text macro is to be inserted at the location in the report. A probability for the text macro to be inserted at the location in the report may be produced based upon, at least in part, the transcript, the text macro, and preceding words in the report. The probability for the text macro to be inserted at the location in the report may be further based upon, at least in part, an encoded representation of an input to the encoder, and an encoded representation of the text macro. The text macro for the report may be displayed differently from non-text macro. Attributes of the text macro for the report may be displayed differently from non-text macro. Any of the text macros may be deleted from the report using a shortcut without requiring individual deletion of each character in content of the text macros.

In another example implementation, a computer program product may reside on a computer readable storage medium having a plurality of instructions stored thereon which, when executed across one or more processors, may cause at least a portion of the one or more processors to perform operations that may include but are not limited to encoding a transcript and text macros into vector representations. A word by word report may be predicted based upon, at least in part, the encoding. An attention mechanism may be queried based upon, at least in part, a decoder state. An attention distribution may be produced over an encoder output. An interpolation of the encoder output may be produced based upon, at least in part, the attention distribution. The interpolation of the encoder output may be input into a decoder for report modeling that may include text macro location and content.

One or more of the following example features may be included. A decoder output may be augmented with a sentinel token, wherein the sentinel token may indicate the text macro is to be inserted at the location in the report. A probability for the text macro to be inserted at the location in the report may be produced based upon, at least in part, the transcript, the text macro, and preceding words in the report. The probability for the text macro to be inserted at the location in the report may be further based upon, at least in part, an encoded representation of an input to the encoder, and an encoded representation of the text macro. The text macro for the report may be displayed differently from non-text macro. Attributes of the text macro for the report may be displayed differently from non-text macro. Any of the text macros may be deleted from the report using a shortcut without requiring individual deletion of each character in content of the text macros.

The details of one or more implementations are set forth in the accompanying drawings and the description below. Other features and advantages will become apparent from the description, the drawings, and the claims.

BRIEF DESCRIPTION OF THE DRAWINGS

Like reference symbols in the various drawings indicate like elements.

DETAILED DESCRIPTION OF THE PREFERRED EMBODIMENTS

Figure 1:
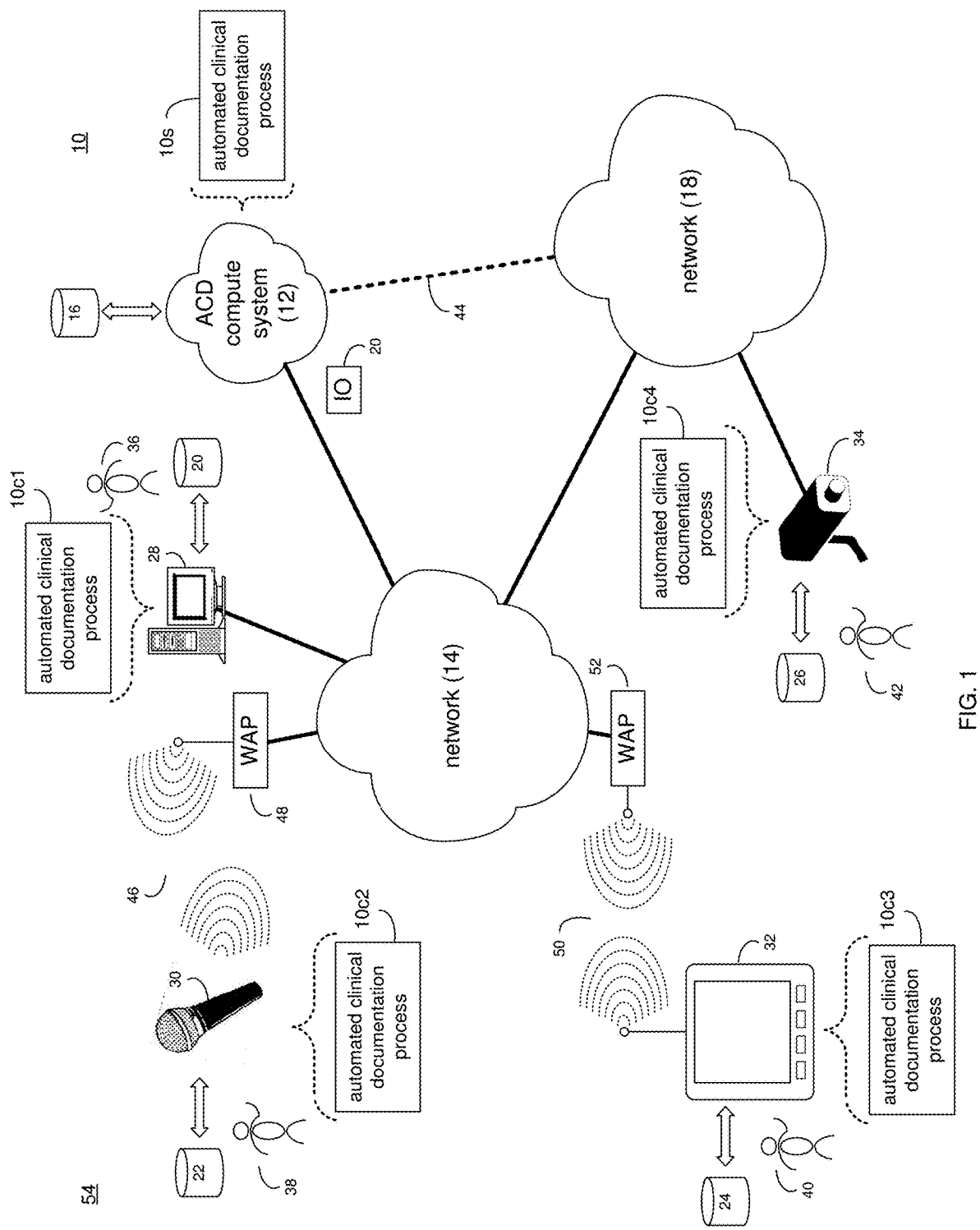
FIG. 1 is a diagrammatic view of an automated clinical documentation computer system and an automated clinical documentation process coupled to a distributed computing network according to one or more example implementations of the disclosure.

System Overview:

Referring to FIG. 1, there is shown automated clinical documentation process 10. As will be discussed below in greater detail, automated clinical documentation process 10 may be configured to automate the collection and processing of clinical encounter information to generate/store/distribute medical records.

Automated clinical documentation process 10 may be implemented as a server-side process, a client-side process, or a hybrid server-side/client-side process. For example, automated clinical documentation process 10 may be implemented as a purely server-side process via automated clinical documentation process 10s. Alternatively, automated clinical documentation process 10 may be implemented as a purely client-side process via one or more of automated clinical documentation process 10c1, automated clinical documentation process 10c2, automated clinical documentation process 10c3, and automated clinical documentation process 10c4. Alternatively still, automated clinical documentation process 10 may be implemented as a hybrid server-side/client-side process via automated clinical documentation process 10s in combination with one or more of automated clinical documentation process 10c1, automated clinical documentation process 10c2, automated clinical documentation process 10c3, and automated clinical documentation process 10c4.

Accordingly, automated clinical documentation process 10 as used in this disclosure may include any combination of automated clinical documentation process 10s, automated clinical documentation process 10c1, automated clinical documentation process 10c2, automated clinical documentation process 10c3, and automated clinical documentation process 10c4.

Automated clinical documentation process 10s may be a server application and may reside on and may be executed by automated clinical documentation (ACD) computer system 12, which may be connected to network 14 (e.g., the Internet or a local area network). ACD computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACD computer system 12 may execute one or more operating systems, examples of which may include but are not limited to: Microsoft Windows Server™; Redhat Linux™, Unix, or a custom operating system, for example.

The instruction sets and subroutines of automated clinical documentation process 10s, which may be stored on storage device 16 coupled to ACD computer system 12, may be executed by one or more processors (not shown) and one or more memory architectures (not shown) included within ACD computer system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from automated clinical documentation process 10s, automated clinical documentation process 10c1, automated clinical documentation process 10c2, automated clinical documentation process 10c3 and/or automated clinical documentation process 10c4 to ACD computer system 12. Examples of IO request 20 may include but are not limited to data write requests (i.e. a request that content be written to ACD computer system 12) and data read requests (i.e. a request that content be read from ACD computer system 12).

The instruction sets and subroutines of automated clinical documentation process 10c1, automated clinical documentation process 10c2, automated clinical documentation process 10c3 and/or automated clinical documentation process 10c4, which may be stored on storage devices 20, 22, 24, 26 (respectively) coupled to ACD client electronic devices 28, 30, 32, 34 (respectively), may be executed by one or more processors (not shown) and one or more memory architectures (not shown) incorporated into ACD client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACD client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACD computer system 12 directly through network 14 or through secondary network 18. Further, ACD computer system 12 may be connected to network 14 through secondary network 18, as illustrated with link line 44.

The various ACD client electronic devices (e.g., ACD client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACD client electronic devices (e.g., ACD client electronic devices 28, 30, 32, 34) may each execute an operating system, examples of which may include but are not limited to Microsoft Windows™, Apple Macintosh™, Redhat Linux™ or a custom operating system, wherein the combination of the various ACD client electronic devices (e.g., ACD client electronic devices 28, 30, 32, 34) and ACD computer system 12 may form modular ACD system 54.

Figure 2:
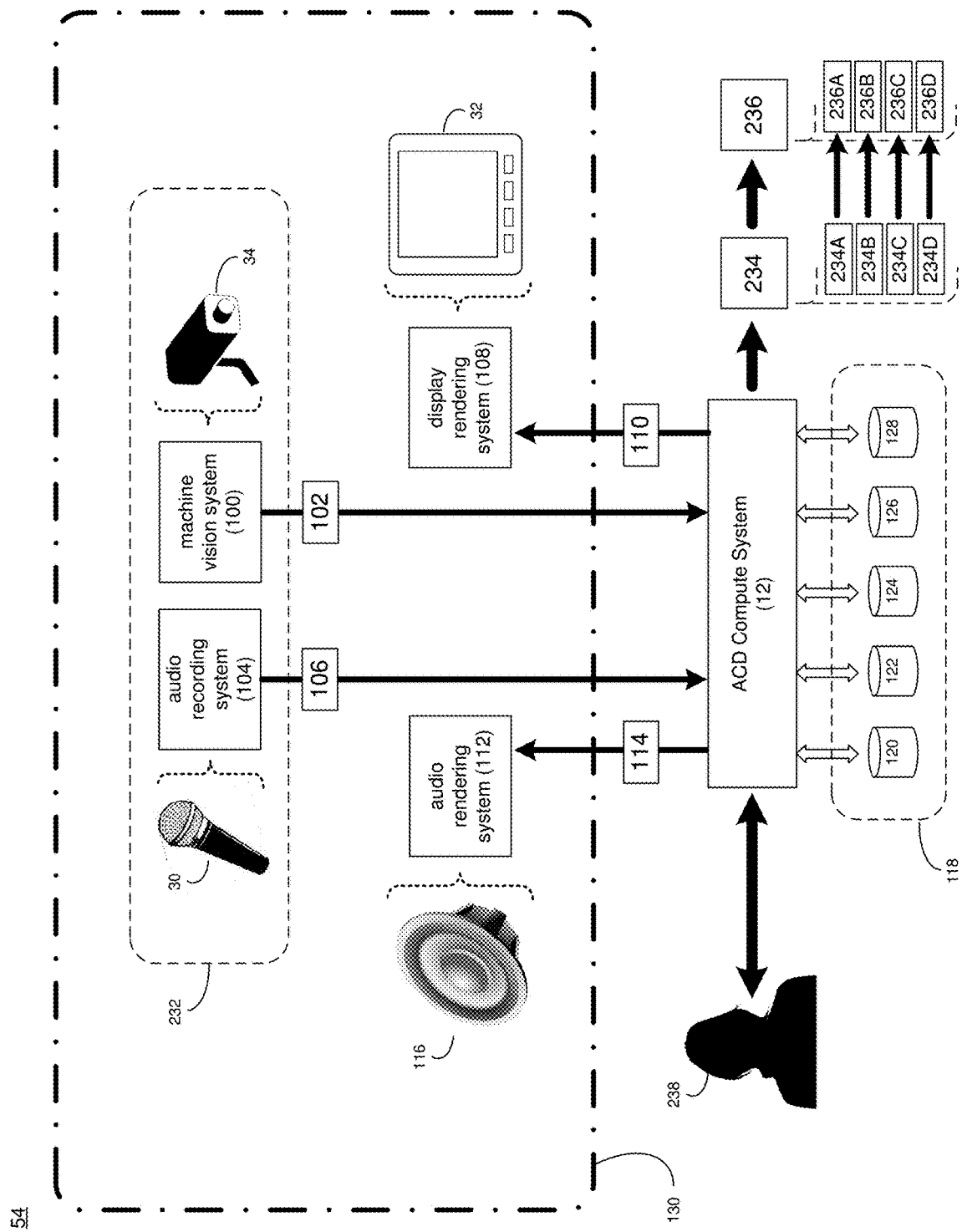
FIG. 2 is a diagrammatic view of a modular ACD system incorporating the automated clinical documentation computer system of FIG. 1 according to one or more example implementations of the disclosure.

Referring also to FIG. 2, there is shown a simplified example embodiment of modular ACD system 54 that is configured to automate clinical documentation. Modular ACD system 54 may include: machine vision system 100 configured to obtain machine vision encounter information 102 concerning a patient encounter; audio recording system 104 configured to obtain audio encounter information 106 concerning the patient encounter; and a computer system (e.g., ACD computer system 12) configured to receive machine vision encounter information 102 and audio encounter information 106 from machine vision system 100 and audio recording system 104 (respectively). Modular ACD system 54 may also include: display rendering system 108 configured to render visual information 110; and audio rendering system 112 configured to render audio information 114, wherein ACD computer system 12 may be configured to provide visual information 110 and audio information 114 to display rendering system 108 and audio rendering system 112 (respectively).

Example of machine vision system 100 may include but are not limited to: one or more ACD client electronic devices (e.g., ACD client electronic device 34, examples of which may include but are not limited to an RGB imaging system, an infrared imaging system, a ultraviolet imaging system, a laser imaging system, a SONAR imaging system, a RADAR imaging system, and a thermal imaging system). Examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Examples of display rendering system 108 may include but are not limited to: one or more ACD client electronic devices (e.g., ACD client electronic device 32, examples of which may include but are not limited to a tablet computer, a computer monitor, and a smart television). Examples of audio rendering system 112 may include but are not limited to: one or more ACD client electronic devices (e.g., audio rendering device 116, examples of which may include but are not limited to a speaker system, a headphone system, and an earbud system).

As will be discussed below in greater detail, ACD computer system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource. While in this particular example, five different examples of datasources 118, are shown, this is for illustrative purposes only and is not intended to be a limitation of this disclosure, as other configurations are possible and are considered to be within the scope of this disclosure.

As will be discussed below in greater detail, modular ACD system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACD client electronic devices (e.g., ACD client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACD client electronic devices (e.g., ACD client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACD client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACD computer system 12 may include a plurality of discrete computer systems. As discussed above, ACD computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACD computer system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Figure 3:
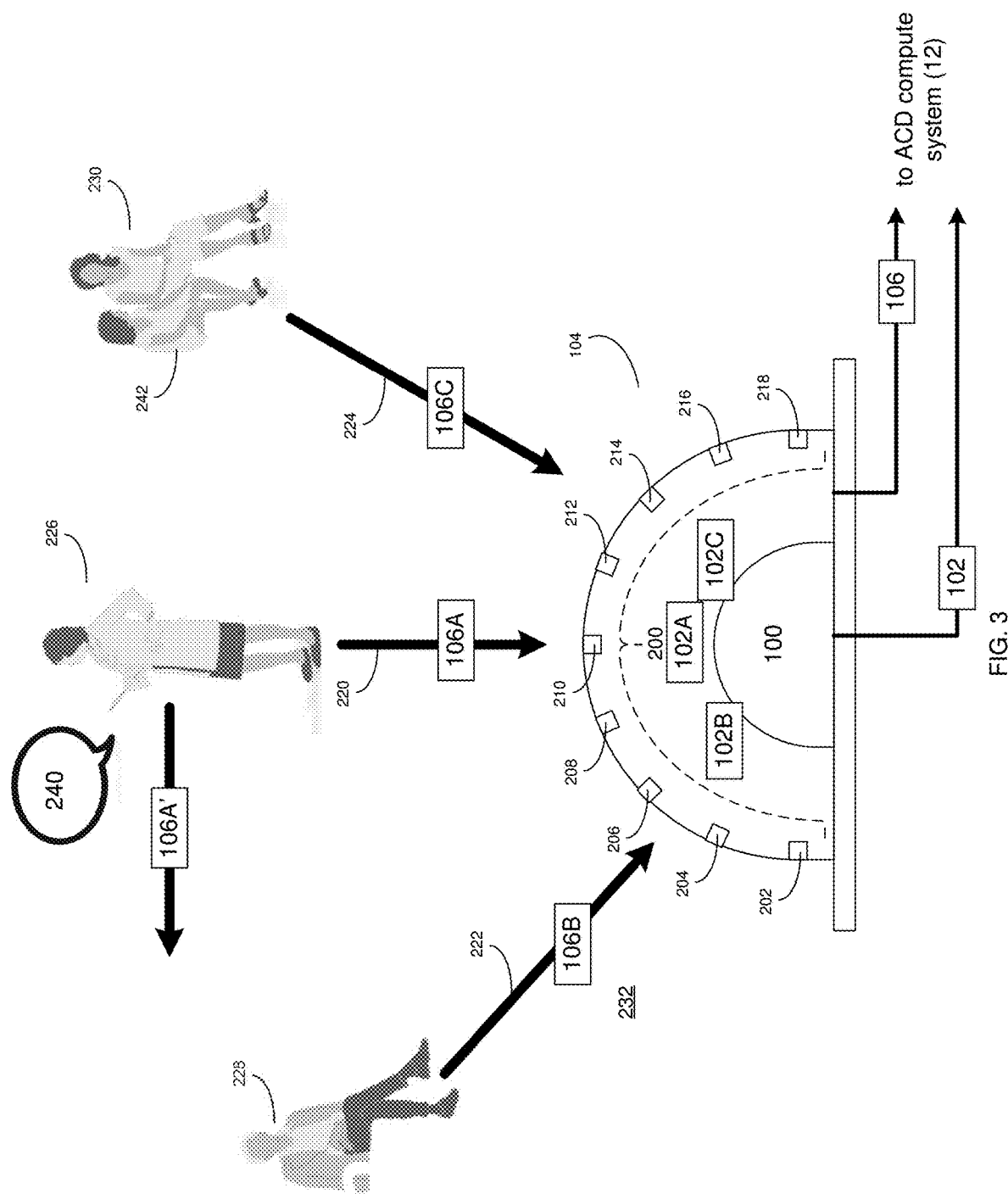
FIG. 3 is a diagrammatic view of a mixed-media ACD device included within the modular ACD system of FIG. 2 according to one or more example implementations of the disclosure.
Figure 4:
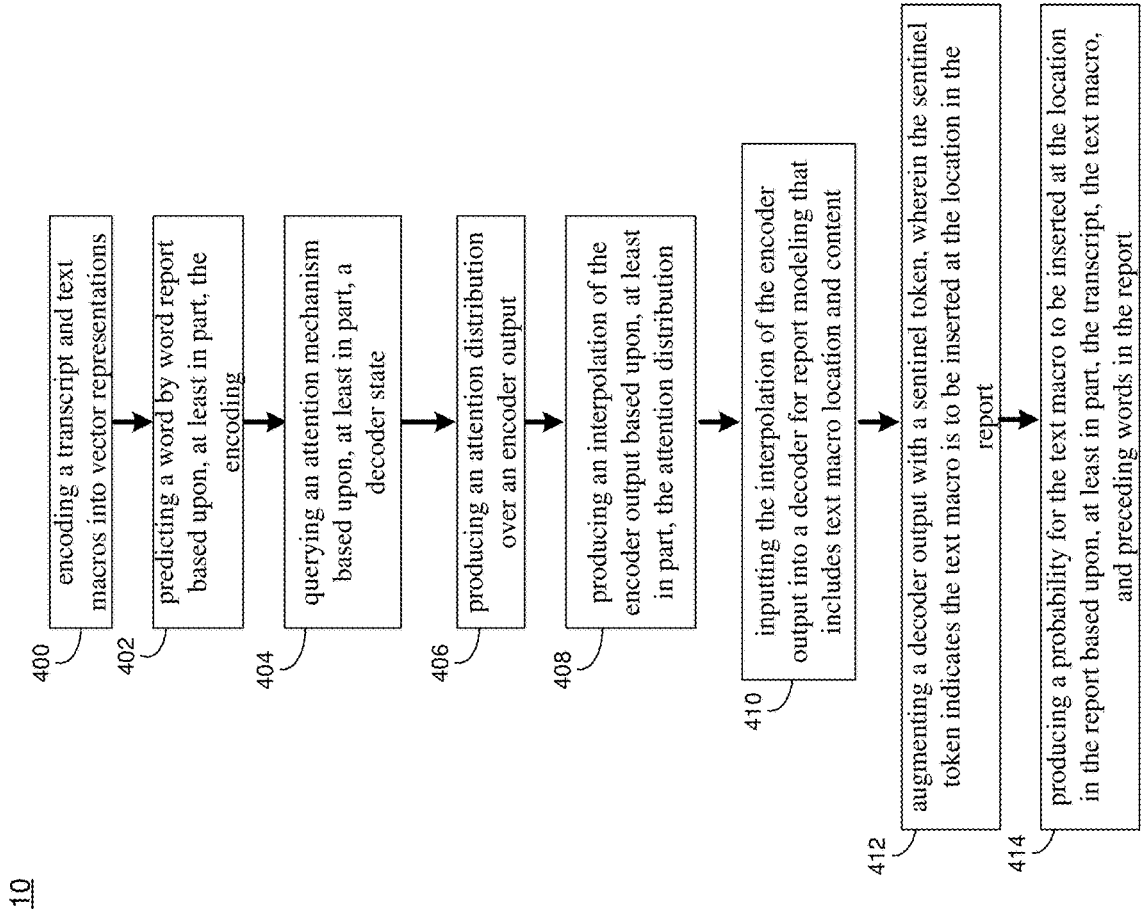
FIG. 4 is a flow chart of one implementation of the automated clinical documentation process of FIG. 1 according to one or more example implementations of the disclosure.
Figure 5:
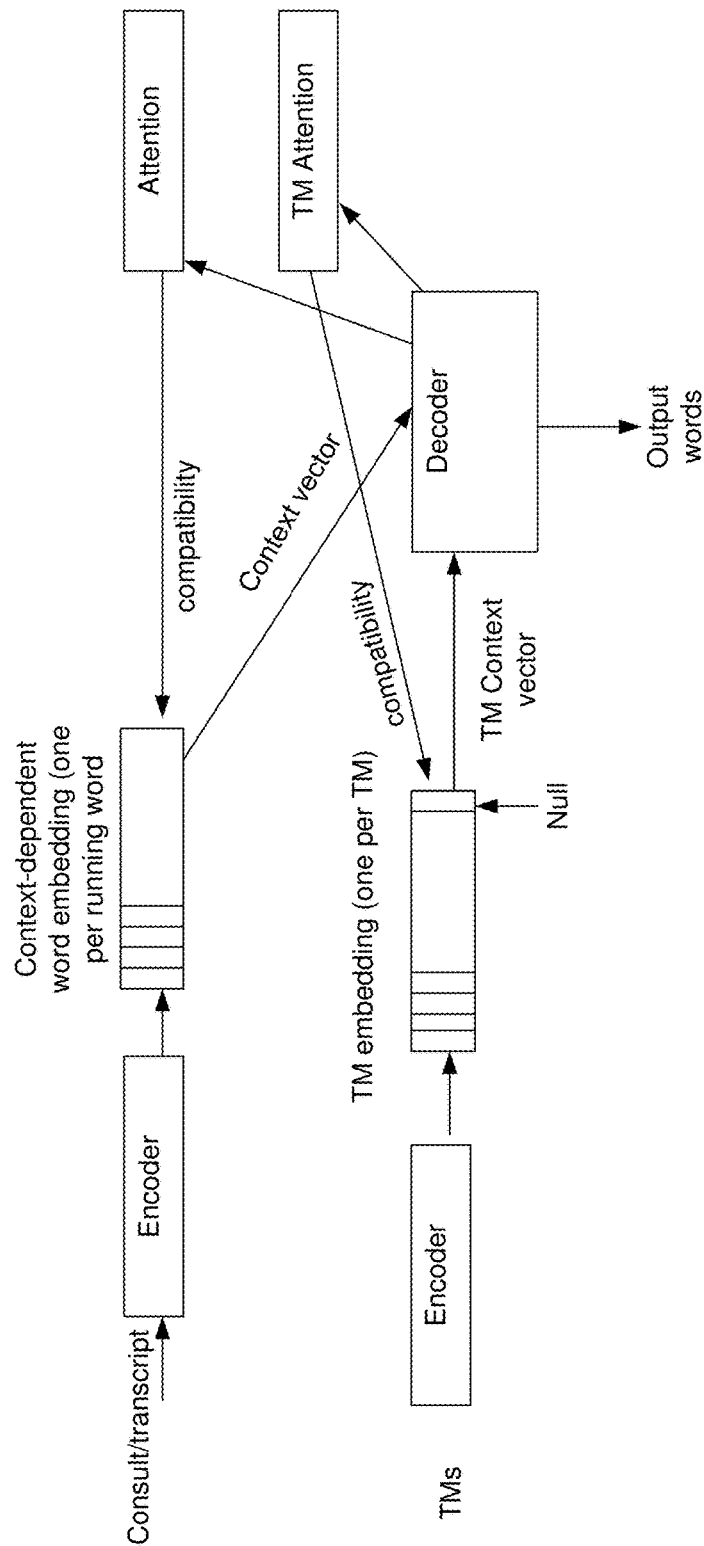
FIG. 5 is a diagrammatic view of an example model architecture of the automated clinical documentation process of FIG. 1 according to one or more example implementations of the disclosure.
Figure 6:
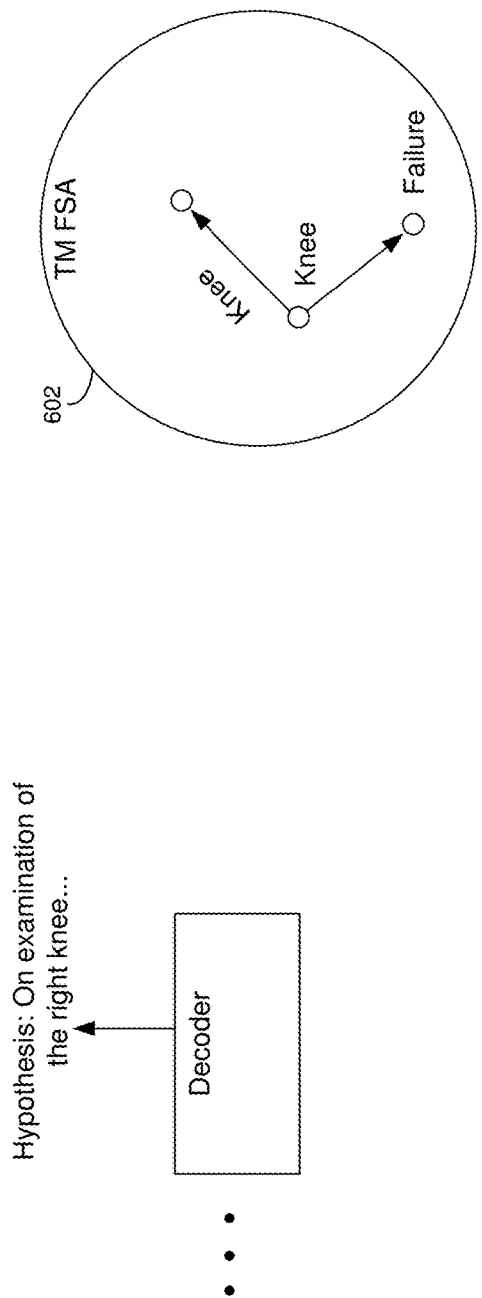
FIG. 6 is a diagrammatic view of an example model inference of the automated clinical documentation process of FIG. 1 according to one or more example implementations of the disclosure.
Figure 7:
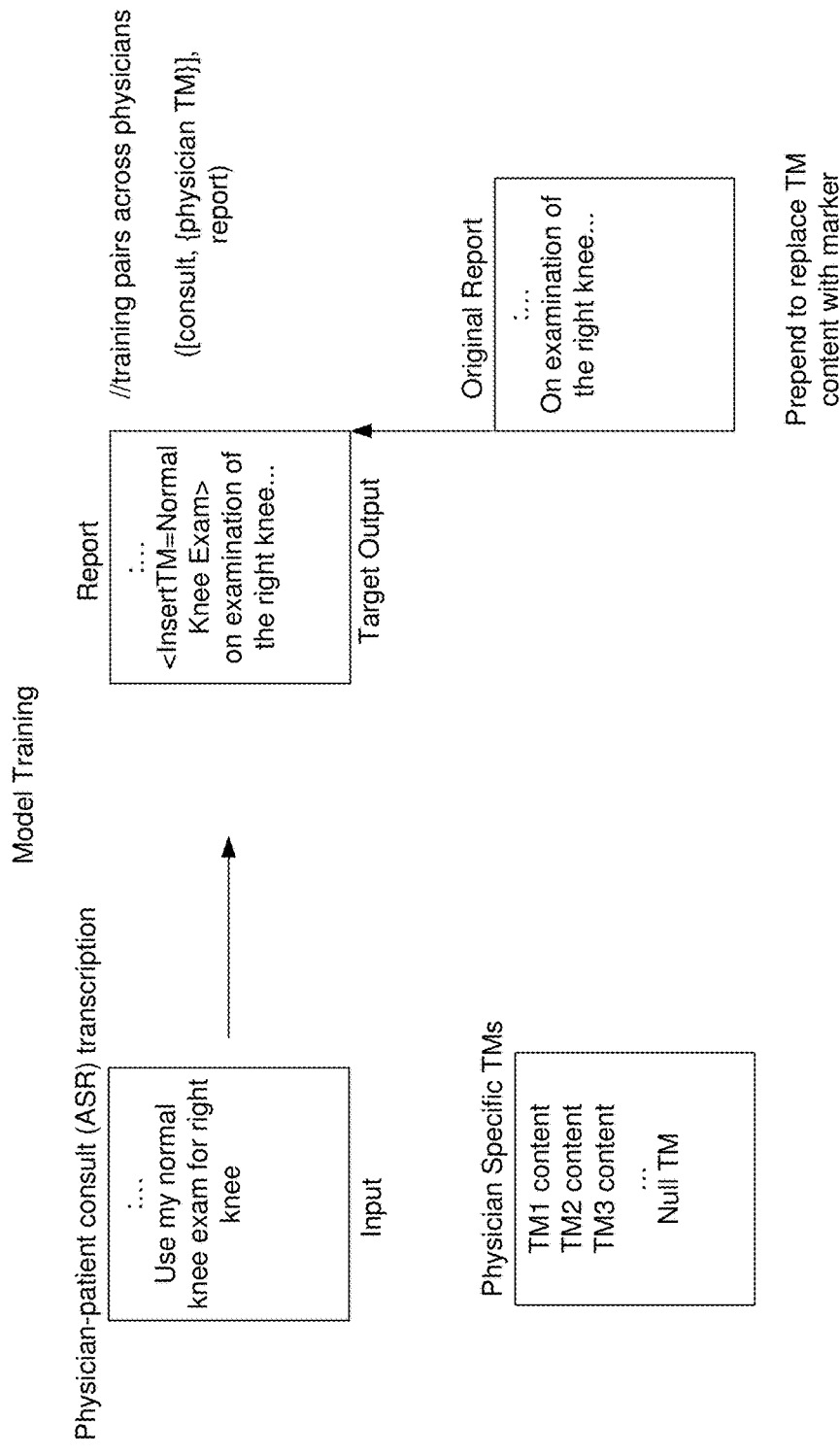
FIG. 7 is a diagrammatic view of an example model training the automated clinical documentation process of FIG. 1 according to one or more example implementations of the disclosure.

Referring also to FIG. 3, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACD system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACD system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, modular ACD system 54 and/or audio recording system 104 may be configured to utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, modular ACD system 54 and/or audio recording system 104 may be configured to utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230). Further, modular ACD system 54 and/or audio recording system 104 may be configured to utilize null-steering precoding to cancel interference between speakers and/or noise.

As is known in the art, null-steering precoding is a method of spatial signal processing by which a multiple antenna transmitter may null multiuser interference signals in wireless communications, wherein null-steering precoding may mitigate the impact off background noise and unknown user interference.

In particular, null-steering precoding may be a method of beamforming for narrowband signals that may compensate for delays of receiving signals from a specific source at different elements of an antenna array. In general and to improve performance of the antenna array, in incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACD device 232. For example, mixed-media ACD device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACD system 54 may be configured to include a plurality of mixed-media ACD devices (e.g., mixed-media ACD device 232) when the above-described clinical environment is larger or a higher level of resolution is desired.

Modular ACD system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACD device 232 (and machine vision system 100/audio recording system 104 included therein) may be configured to monitor one or more encounter participants (e.g., encounter participants 226, 228, 230) of a patient encounter.

Specifically, machine vision system 100 (either as a stand-alone system or as a component of mixed-media ACD device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACD computer system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACD system 54 (and/or mixed-media ACD device 232) is configured, ACD computer system 12 may be included within mixed-media ACD device 232 or external to mixed-media ACD device 232.

As discussed above, ACD computer system 12 may execute all or a portion of automated clinical documentation process 10, wherein the instruction sets and subroutines of automated clinical documentation process 10 (which may be stored on one or more of e.g., storage devices 16, 20, 22, 24, 26) may be executed by ACD computer system 12 and/or one or more of ACD client electronic devices 28, 30, 32, 34.

As discussed above, automated clinical documentation (ACD) process 10 may be configured to automate the collection and processing of clinical encounter information to generate/store/distribute medical records. ACD process 10 may be configured to obtain encounter information (e.g., machine vision encounter information 102 and/or audio encounter information 106) of a patient encounter (e.g., a visit to a doctor's office) of at least a first encounter participant, wherein the encounter information may include audio encounter information obtained from at least a first encounter participant (e.g., encounter participant 228, 226, 230, and/or 242). ACD process 10 may further be configured to process the encounter information (e.g., machine vision encounter information 102 and/or audio encounter information 106) obtained from at least the first encounter participant, e.g., to generate an encounter transcript (e.g., encounter transcript 234) and/or generate a user interface displaying a plurality of layers associated with the audio encounter information obtained from at least the first encounter participant. In some implementations, ACD process 10 may process at least a portion of the encounter transcript (e.g., encounter transcript 234) to populate at least a portion of a medical record (e.g., medical record 236) associated with the patient encounter (e.g., the visit to the doctor's office). Encounter transcript 234 and/or medical record 236 may be reviewed by a medical professional involved with the patient encounter (e.g., a visit to a doctor's office) to determine the accuracy of the same and/or make corrections to the same.

As noted above, ACD process 10 may process the audio encounter information obtained from at least the first encounter participant. In some implementations, processing the first audio encounter information may include defining linkages between each of the plurality of layers associated with the audio encounter information. For example, the first layer of the plurality of layers may be an audio signal associated with the audio encounter information (e.g., complete audio of the encounter, encompassing and clearly delineating each participant), wherein the second layer of the plurality of layers may be a transcript associated with the audio encounter information (e.g., a diarized audio transcript (verbatim) for each participant in the encounter), and wherein the third layer of the plurality of layers may be a medical report associated with the audio encounter information (e.g., a draft medical report in the appropriate clinical output format). In some implementations, additional layers may include, e.g., the above-noted machine vision-based recording of the encounter, including various signal formats and features, and discrete, standardized, actionable data resulting from the encounter, including, but not limited to medication plans (for example, in RxNorm) or lab orders (for example, LOINC) or diagnoses (for example, ICD10, CPT etc). In the example, the signals captured from the encounter information may be processed into at least the above-noted three separate, yet closely linked and interdependent layers. In some implementations, speech may be augmented with additional information (e.g., accompanying video signal, physician metadata (such as their set of text macros) and patient/visit metadata (e.g., name/age/chief complaint) that may already be available from EHR or the patient intake process).

In some implementations, ACD process 10 may include an ASR portion that may process the audio encounter information producing an approximate (e.g., diarized) verbatim transcript along with alignment information indicating the audio interval corresponding to each transcript word. In some implementations, a deep learning (e.g., sequence to sequence) model associated with ACD process 10 may convert the transcript to a medical report. It will be appreciated that various attribution techniques may be employed by ACD process 10 that may effectively softly assign responsibility for a given output (e.g., medical report) word to input (e.g., conversation transcript) words (e.g. attention weights, integrated gradient, etc.) according to the model. As a result, this may provide a soft mapping from the transcript word positions to report word positions. In some implementations, the input word position assigned maximal attribution for a given output word may be interpreted as being aligned (linked) to that output (e.g., when a hard mapping is required). Based on the ASR time alignment, a word in the draft medical report, aligned to a word in the ASR conversation transcript, may now be associated with an audio time interval of the associated audio signal of the audio encounter information.

In some implementations, ACD process 10 may also may link (i.e., align) the ASR conversation transcript words with the draft medical report words. For transcript words that may have maximal attribution value for some set of medical report words, ACD process 10 may link them with the first word in that set. For the remaining transcript words, ACD process 10 may link them to the same word that the nearest preceding (or if none, nearest subsequent) conversation transcript word is linked to.

In some implementations, a visual recording (e.g., video stream of the patient encounter), if available, may also be a layer and may be time indexed and thus a given point in the recording may be associated with the same time in the audio recording and thus a conversation transcript word and draft report word. In some implementations, if discrete, standardized, actionable data is produced as a second (parallel) output sequence of the sequence to sequence model, then a similar model output attribution technique may be used to align tokens in this actionable data with the ASR conversation transcript words, and thus the audio intervals.

Generally, text macros (TMs) may be described as physician (or other user) customized boilerplate text (and/or images, tables, etc.) optionally with embedded categorical and/or numeric choice lists or free text "blanks" (also referred to as "attributes"). TMs may sometimes also be generically referred to as "autotext". Physicians may find TM particularly useful, since they allow them to precisely control report (scribed) content with minimal communication effort (e.g., physician says "right knee would be the normal knee exam template" and "On examination of the knee, there is no edema, no effusion, no ecchymosis, and no erythema. There is no focal tenderness. Range of motion is full and without pain. Patellar alignment appears normal. No laxity on varus and valgus stress. Medial and lateral McMurray test is negative. Anterior drawer is negative. Posterior drawer is negative. Patellar grind test is negative." is entered in the report with "right" populating the blank).

Typically, the naïve approach would treat TM content like any other content both for modeling and UX purposes. Specifically, in drafts generated by an AI system, the TM content would not be differentiated from any other draft content (making it difficult for a (scribe or physician) reviewer to determine if the correct TM had been identified and faithfully rendered (and thus fulfilled the physician's intent)) and no special means would be provided for efficiently recovering from incorrectly inserted TM. One would also rely on the model to associate TM references (e.g., "use my normal right knee exam template") with the TM content directly (e.g., "On examination of the right knee, there is no edema, no effusion, no ecchymosis, and no erythema . . . ") requiring a significant number of pairs for each TM instance per physician to be observed in model training and providing limited ability to learn from training instances across physicians or to assert the TM content is fully faithfully rendered. Such training would need to be repeated if any change in TM content were made.

As such, as will be discussed below, the present disclosure may help to (partially or fully) automate the scribing process through the use of artificial intelligence (AI). In particularly, the present disclosure may enable the learning of a sequence to sequence model which maps from an automatically (via ASR) generated approximate transcript of a physician-patient consult (and any associated preceding/subsequent audio/video content from physician) to a draft medical report. (It may also be possible that a model goes directly from audio (and potentially video) signal to the report and also that the model has access to other relevant info sources). With automation, this enables the continued support and indeed accelerated TM mechanism. This is challenging since the set of TMs and their content may be physician specific and in principle they may update the set and the content for a specific TM over time, and yet the amount of physician specific (e.g., consult, report) examples for model training may be limited (especially for a new site or physician). Accordingly, the present disclosure may maximize system performance (e.g., accurately render physician-intended TMs in the draft report) as a function of available per-physician data, and maximize the efficiency with which a scribe or physician may verify or correct TMs and their attributes inserted (or omitted) from the draft report.

The present disclosure may improve upon a baseline approach which would simply predict TM content along with non-Text macros content word by word and not distinguish among these content types in the report draft. Specifically, as will be discussed below, the present disclosure may accomplish this by decoupling modeling and rendering of TMs which allows sharing of the modeling burden across physicians (with differing text macros content and sets), to facilitate verification/correction by highlighting TM spans, identifiers and attributes in draft reports, and to efficiently recover from omissions by providing a ranked (e.g., drop down) list of TM alternates for a given report (e.g., section).

As will also be discussed below, prediction of an TM, which TM and then rendering of its content may therefore be decoupled, and TMs may be atomically represented by an embedding reflecting their content. This may allow the model to leverage TM usage across physicians to improve performance for a given physician, taking advantage of the common ways that TMs are implicitly referred to (e.g. "use my . . . template") and the significant overlap (without being an exact match) in TM content for a particular common finding, etc. In a particular embodiment, this may be accomplished via a dedicated TM Encoder which operates over each TM content for a physician, deriving an embedding per (physician) TM; this is connected to a Decoder via a dedicated TM Attention module. During training, the decoder output (e.g., medical report) target (and thus vocabulary) may include a sentinel token when and where an TM should be inserted with the probability of a specific TM given by the TM attention distribution. Finally during decoding, a model hypothesis may be explicitly constrained to faithfully generate TM content once it predicts a specific TM instance. As a result the system may be able to be significantly more data efficient, achieving high performance (especially in the prediction and rendering of TMs) per physician with limited physician-specific training examples (e.g., ([consult, {physician Text macross}], report) pairs). Moreover, as will be discussed further below, report generation may be conditioned not only on the transcript, but on the (current) TMs for the physician. These may be separately encoded and a separate attention mechanism may be used to determine weights (e.g., via compatibility with preceding decoder state) with which to interpolate these encodings with result fed into the decoder (along with (attention-weighted) interpolation of transcript encodings). It will be appreciated that while the present disclosure involves starting with a conversational transcript, it will be appreciated that the present disclosure may also encode (and map from) conversation audio directly.

As discussed above and referring also at least to the example implementations of FIGS. 4-8, ACD process 10 may encode 400 a transcript and text macros into vector representations. ACD process 10 may predict 402 a word by word report based upon, at least in part, the encoding. ACD process 10 may query 404 an attention mechanism based upon, at least in part, a decoder state. ACD process 10 may produce 406 an attention distribution over an encoder output. ACD process 10 may produce 408 an interpolation of the encoder output based upon, at least in part, the attention distribution. ACD process 10 may input 410 the interpolation of the encoder output into a decoder for report modeling that may include text macro location and content.

In some implementations, to allow for more data efficient (e.g., limit the data burden per physician, even with customized text macros (TMs)) and more accurate TM modeling, the present disclosure may decouple TM modeling from the text rendering, and TM content (which may have significant commonalities across physician but may generally be distinct) may be used as opposed to only its physician-supplied name to predict the TM. The present disclosure may also factor out modeling language physicians use to communicate an TM of any kind that may be used and at what position they are inserted in a final report (e.g., post transcript generation).

In some implementations, ACD process 10 may encode 400 a transcript and text macros into vector representations, and may predict 402 a word by word report based upon, at least in part, the encoding. For example, referring at least to the example implementation of FIG. 5, an example model architecture 500 is shown, and referring at least to the example implementation of FIG. 6 and example model inference 600 is shown. Notably, while the present disclosure may be described within the context of an Encoder-Decoder with Attention (e.g., sequence-to-sequence (seq2seq)) model, other similar embodiments are possible. For instance, in a "general" approach, ACD process 10 may, e.g., via an Encoder subnetwork (e.g., a bidirectional recurrent neural network or RNN), encode 400 the input transcript (e.g., generated from the above-noted patient encounter) into a sequence (e.g., same length as the input) of vector representations. ACD process 10 may, e.g., via an auto-regressive (e.g., RNN) Decoder subnetwork, predict the draft report word by word (e.g., with a probability distribution over output vocabulary words estimated for each step). For example, in "greedy" decoding, the decoder (e.g., via ACD process 10) may produce a probability over a fixed vocabulary of words (including the sentinel <InsertText-Macros> token) at each time step and may select the token with maximal probability as the one to output and to (e.g., auto-regressively) feed back into the decoder, along with the (attention-weighted, weights computed as a function of decoder state from previous time step) interpolated encoder output, or context vector, and (TM attention-weighted) interpolated TM encoder output, or TM context vector, for the next time step. In beam (or k-best) decoding, instead of only maintaining a single hypothesis of the report so far, the system may maintain the k-best hypotheses (e.g., a tuple of (logProbability, [hypothesized text so far], decoder state) and consider extensions of each of them at each step and retain the overall k-best scoring (in terms of logProbability) ones. It will be appreciated that a convolutional or transformer architecture may be used in place of or in conjunction with the above-noted RNN.

The Decoder may be connected to the Encoder output via an Attention mechanism. In some implementations, there may be a distinct TM Encoder subnetwork (e.g., bidirectional RNN or biRNN). It may be applied to the TM content (e.g., with embedded attributes indicated by blank symbols) of each TM registered for the physician of a given consult, yielding a fixed length vector representation (e.g., concatenation of first/last hidden state from the biRNN). This may generally be referred to as the TM embedding.

While in training (and referring also to the example implementation of FIG. 7 where example model training 700 is shown), it may be unnecessary to constrain the model to predict the full and valid TM content with a probability 1 (i.e., certainty) conditioned on predicting that a specific TM (e.g., via the above-noted sentinel token) should be inserted, ACD process 10 may apply this constraint at inference. For example, ACD process 10 may use a finite state automaton (FSA) (e.g., TM FSA 602 from FIG. 6) to limit the valid extensions of a (draft report) hypothesis considered by the Decoder to ensure the complete TM content is generated once it chooses to insert that TM, and that all embedded attribute constraints are respected. The FSA may reflect changes in the TM content that were not present when the sequence-to-sequence model was trained. Indeed, it is possible to apply the sequence to sequence model to a new physician or new set of customized TMs and expect reasonable performance.

In some implementations, ACD process 10 may query 404 an attention mechanism based upon, at least in part, a decoder state, and may produce 406 an attention distribution over an encoder output. For instance, ACD process 10 may use the preceding Decoder state (e.g., initialized to a learned vector) as a query 404 to the attention mechanism, which via a (e.g., softmax) normalized compatibility function (e.g., dot-product) applied to the query and each Encoder output in turn, may enable ACD process 10 to produce 406 an attention distribution (or weights) over the Encoder output. For example, at each time step, the decoder (e.g., via ACD process 10) may take as input the preceding predicted word, a context vector and a TM context vector and may produce a new hidden state which may be both used as the basis for producing a probability distribution over the output vocabulary (e.g., via affine transformation plus softmax) and as an input to the attention mechanisms for the transcript and TM encoders' outputs. If the transcript encoder output is denoted as vectors TE1, TE2, . . . and the decoder state at time t as Dt then ACD process 10 may compute compatibility[i]=F (Dt,TE[i]) for each i, (F may be as simple as dotproduct or may have learnable parameters, e.g., a single layer MLP) and then interpolationWeight[i]=exp(compatibility[i])/Sum{i'}exp(compatibility[i']), e.g., softmax normalization, and finally contextVector=Sum{i}interpolationWeight[i]*TE[i] which may be fed into the decoder to determine Dt+1 and the corresponding output vocabulary probability distribution. An analogous procedure may be done with the TM encoder output and TM attention mechanism (e.g., potentially distinctly parameterized "F"), again as a function of the decoder state (Dt). It will be appreciated that the above expressions may vary without departing from the scope of the disclosure (e.g., a temperature term, a windowed interpolation, etc.). As such, the above expressions should be taken as example only and not to otherwise limit the scope of the present disclosure.

In some implementations, ACD process 10 may produce 408 an interpolation of the encoder output based upon, at least in part, the attention distribution, and may input 410 the interpolation of the encoder output into a decoder for report modeling that may include text macro location and content. For example, the above-noted weights may be used by ACD process 10 to produce 408 a linear interpolation of the Encoder output (e.g., a context vector), which may be fed (or input 410) as an additional input to the Decoder (e.g., in addition to the previous word predicted by the Decoder). In some implementations, ACD process 10 may further learn a fixed length vector representation (e.g., null TM embedding) corresponding to no TM being relevant. As noted above, ACD process 10 may use a distinct TM Attention mechanism, where a Decoder state may be used as a query to this mechanism, which via a (e.g., softmax) normalized compatibility function (e.g., dot-product) applied to the query and each TM embedding in turn, may yield an TM attention distribution (e.g., weights). These weights may be used by ACD process 10 to similarly produce the linear interpolation of the TM embeddings (e.g., an TM context vector), which may be fed as an additional input to the Decoder. It will be appreciated that while a linear interpolation is described, other non-linear interpolations may also be used without departing from the scope of the present disclosure.

In some implementations, ACD process 10 may augment 412 a decoder output with a sentinel token, wherein the sentinel token may indicate the text macro is to be inserted at the location in the report, and in some implementations, ACD process 10 may produce 414 a probability for the text macro to be inserted at the location in the report based upon, at least in part, the transcript, the text macro, and preceding words in the report, and in some implementations, the probability for the text macro to be inserted at the location in the report may be further based upon, at least in part, an encoded representation of an input to the encoder (e.g., transcript and/or audio if being done on a single network and/or visual signal (or derivation of it)), and an encoded representation of the text macro. For example, ACD process 10 may augment 412 the Decoder output vocabulary with a sentinel token indicating an TM should be inserted at that point (e.g., <InsertTextMacros>) and thus at each step ACD process 10 may produce 414 a probability for this event given the preceding words (and TM) predicted for the report (section) and input. This may allow the model to capture those words and phrases like "use my template" used across physicians, which are likely to trigger an TM. The probability estimate for a specific TM (e.g., conditioning on probability of inserting one) may be given by the above-noted TM attention distribution (e.g., re-scaled to ignore the weight for the null TM embedding). Thus, this may be conditioned on the TM content which may have some commonalities across physicians (thus facilitating learning across physicians without requiring a common set of TMs or TM content). In some implementations, the model training data may be prepared such that in the target reports, explicit markers for insertion of specific TMs may be included. As such, ACD process 10 may compute, e.g., (supervised) cross-entropy loss (or other losses such as, e.g., used for reinforcement learning) as per usual. As noted above, while the present disclosure involves starting with a conversational transcript, it will be appreciated that the present disclosure may also encode (and map from) conversation audio directly. Additionally, it will be appreciated that several macros may be used within one decoder output sequence without departing from the scope of the present disclosure.

In some implementations, if and when a scribe (or other user) chooses to insert a Text macros at a given point in report (e.g., because the draft TM from the system was wrong), ACD process 10 may use the system to pre-populate any embedded attributes, which the scribe may then verify. This may be accomplished by applying the same model which creates draft reports, but now constrained to insert the selected TM at that point in the draft.

It will be appreciated that the present disclosure need not be interpreted narrowly in that it only applies to a "greedy" (e.g., always choose maximally likelihood hypothesis extension) Decoding process. For instance, beam decoding may also be used. Similarly, while a generic sequence-to-sequence model is described, the present disclosure may apply equally well to, e.g., models extended with a specific copy-from-input mechanism. Furthermore, it will be appreciated that the present disclosure may utilize a "decoder only approach" where a decoder, being fed the encounter and set of text macros as input, may implicitly encode them layer by decoder layer, and in the case of a transformer architecture, self-attention heads attending to encoded macro or encounter content as appropriate, with a specific head in the final self-attention layer designated as providing the distribution among text macros, in the case of the sentinel text macro insertion token being predicted (and accruing corresponding loss when targeted in training).

A naive UX generally does not distinguish TM spans from non-TM text. This may make it burdensome for the reviewer to determine if embedded TM content exactly matches the physician supplied custom text (as the reviewer will generally not have committed it to memory and it may require linearly perusing the entire span). As such, as will be discussed below, ACD process 10 may differentiate an TM span and may also differentiate any attributes in the TM span (e.g., "right").

For example, in some implementations, the text macro for the report may be displayed differently from a non-text macro. For instance, and referring to the example implementation of FIG. 8, and example UX 800 is shown. UX 800 may be used for facilitating verification and/or correction or deletion of TM content (e.g., by a scribe or physician or other user). For example, in report 802, it can be seen that TM content (e.g., "there is no edema, no effusion, no ecchymosis, and no erythema. There is no focal tenderness. Range of motion is full and without pain. Patellar alignment appears normal. No laxity on varus and valgus stress. Medial and lateral McMurray test is negative. Anterior drawer is negative. Posterior drawer is negative. Patellar grind test is negative." is differentiated from non-TM content. In the example, the visual differentiation is a lighter font color; however, it will be appreciated that other techniques to differentiate TM content from non-TM content (e.g., highlight, bold, italic, shading, transparency, etc.) may also be used.

Figure 8:
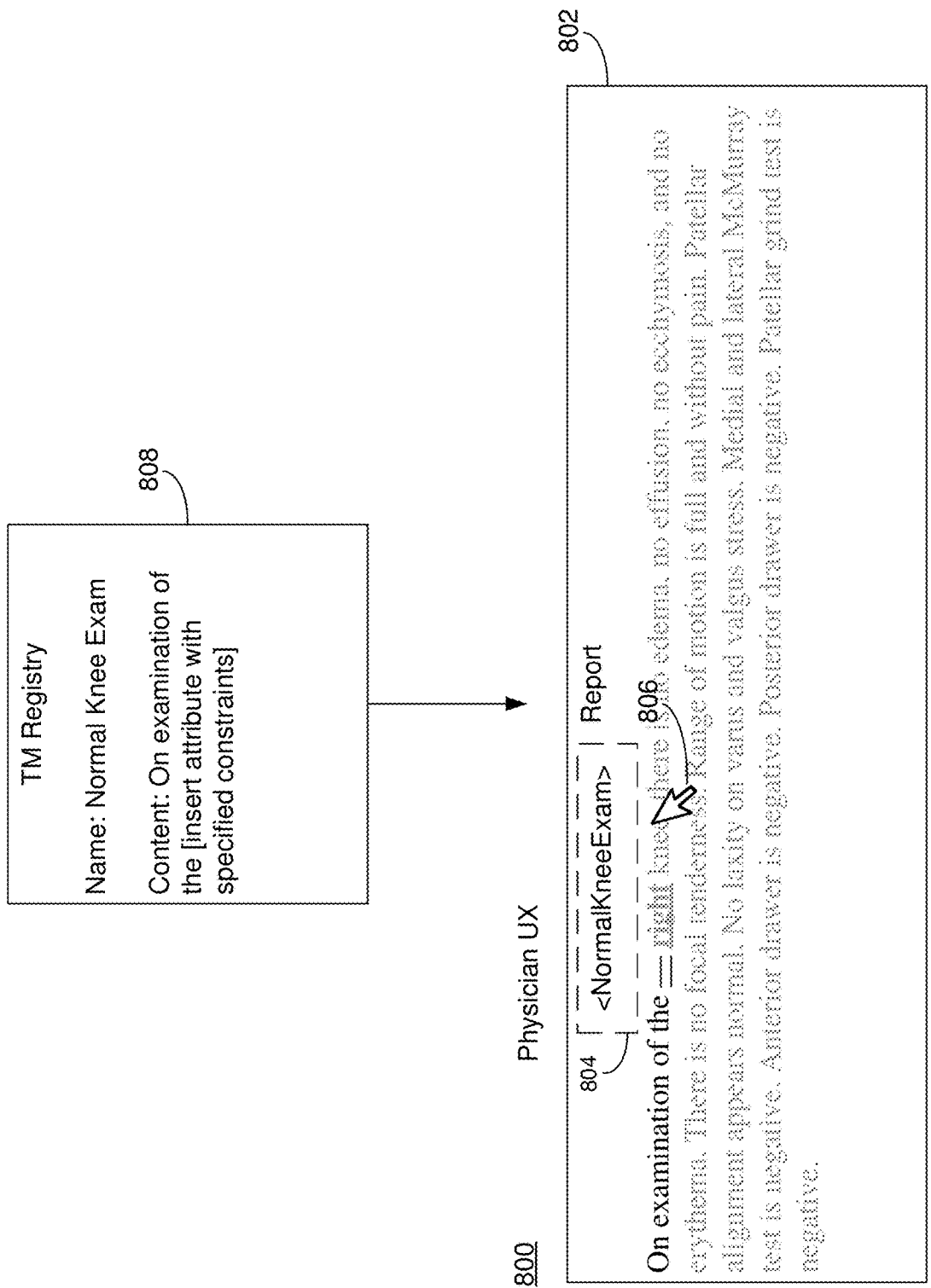
FIG. 8 is a diagrammatic view of an example user interface of the automated clinical documentation process of FIG. 1 according to one or more example implementations of the disclosure.

In some implementations, attributes of the text macro for the report may be displayed differently from a non-text macro. For example, as shown in FIG. 8, any attributes in the TM span (e.g., "right") may also be differentiated visually, again using a distinct color or font, shading, transparency, etc.). In some implementations, ACD process 10 may indicate the (physician-supplied) TM name (e.g., "normal knee exam"), e.g., via markup preceding the TM span (e.g., <NormalKneeExam>) that is understood not to be uploaded to the EHR. For instance, as shown in FIG. 8, the name of the particular TM inserted at a position may be directly observable via object 804 (e.g., when a user hovers cursor 806 over the TM span or inserted non-printable markup, (e.g., <NormalKneeExam>) and any changes from the TM content may also be readily indicated (e.g., via color, strike-out, shading, transparency, etc.). For example, as shown in FIG. 8, "On examination of the _right knee" may be changed to "On examination of the =right knee" showing the strikeout of the blank ("_") and bolding of the "right". That is, the TM content has "On the examination of the _knee" with the expectation that the "_" is an attribute to be filled in. In the example, ACD process 10 has decided to use "right" (based on transcript) and to make it clear that ACD process 10 has replaced the "_" with "right" strikeout "_" and bold/color "right" (but not "knee" which may be denoted in the same font as the rest of the TM boiler plate (though still distinguished from non-TM content). As such, ACD process 10 may distinguish TM spans from non-TM spans, but then within the TM span, highlight boiler plate content which was removed (e.g., "_" or (right|left)) and added (e.g., right).

In some implementations, to facilitate this rendering, a structured interface may be provided for physicians or (site) admins (or other users) to enter custom TMs indicating the TM name, boilerplate content and any embedded categorical choice lists (e.g., right vs left), number ranges and free text fields in a machine readable fashion (e.g., user must click Insert→CategoryChoiceList, enter the categories when prompted and click Ok to enter the category choice list at the insertion point in the TM content, rather than in plain text choose an arbitrary means for communicating to a human scribe that such a choice should be indicated, e.g., via "right|left", "rightOrleft", "right/left", "(right|left)", etc). For example, an TM registry interface for an TM registry (e.g., TM registry 808) may be used so that the location of any embedded attributes and any constraints on their values (e.g., alternation, such as right or left, or numeric range, etc.) may be indicated in a standard machine readable fashion. In some implementations, if a new TM is manually inserted during review, any embedded attributes may be automatically filled in prior to rendering using the same (or different) model used to generate the draft report but constrained to that specific TM at that insertion point in the draft (e.g., with Decoder left context set to that draft prefix).

Any of the text macros may be deleted from the report using a shortcut without requiring individual deletion of each character in content of the text macros. For example, upon review, the span of the inserted TM text may be deleted if necessary with a single "keystroke" (e.g., mouse click or shortcut). That is, the entire TM span in a single text macros may be deleted, but without requiring each character to be deleted in turn or first selecting the TM in its entirety and then pressing the delete button, as is standard. For instance, pressing the delete key applied when the cursor (or other object) is in front of TM name markup may remove the markup and the entire TM span.

It will be appreciated that while the present disclosure is used for medical review, non-medical review purposes may also be used without departing from the scope of the present disclosure. As such, the user of reviewing medical reports should be taken as example only and not to otherwise limit the scope of the present disclosure.

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, not at all, or in any combination with any other flowcharts depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method comprising:
   encoding, by a computing device, a transcript and text macros into vector representations;
   predicting a word by word report based upon, at least in part, the encoding;
   querying an attention mechanism based upon, at least in part, a decoder state;
   producing an attention distribution over an encoder output of the encoding based upon, at least in part, the querying of the attention mechanism;
   producing an interpolation of the encoder output as a context vector based upon, at least in part, the attention distribution;
   inputting both the context vector and a predicted word of the predicted word by word report as inputs into a decoder for report modeling, wherein an output of the decoder includes a location and content of text of a first text macro of the text macros associated with the context vector; and
   outputting the text of the first text macro associated with the context vector in the location of a report.

2. The computer-implemented method of claim 1 further comprising augmenting the decoder output with a sentinel token, wherein the sentinel token indicates the first text macro associated with the context vector is to be inserted at the location in the report.

3. The computer-implemented method of claim 2 further comprising producing a probability for the first text macro associated with the context vector to be inserted at the location in the report based upon, at least in part, the transcript, the first text macro associated with the context vector, and preceding words that precede the first text macro associated with the context vector in the report.

4. The computer-implemented method of claim 3 wherein the probability for the first text macro associated with the context vector to be inserted at the location in the report is further based upon, at least in part, an encoded representation of an input to an encoder, and an encoded representation of the first text macro associated with the context vector.

5. The computer-implemented method of claim 4 wherein the first text macro associated with the context vector for the report is displayed differently from non-text macro.

6. The computer-implemented method of claim 4 wherein attributes of the first text macro associated with the context vector for the report are displayed differently from non-text macro.

7. The computer-implemented method of claim 4 wherein any of the text macros is deleted from the report using a shortcut without requiring individual deletion of each character in content of the text macros.

8. A computer program product residing on a non-transitory computer readable storage medium having a plurality of instructions stored thereon which, when executed across one or more processors, causes at least a portion of the one or more processors to perform operations comprising:
   encoding a transcript and text macros into vector representations;
   predicting a word by word report based upon, at least in part, the encoding;
   querying an attention mechanism based upon, at least in part, a decoder state;
   producing an attention distribution over an encoder output of the encoding based upon, at least in part, the querying of the attention mechanism;
   producing an interpolation of the encoder output as a context vector based upon, at least in part, the attention distribution;

inputting both the context vector and a predicted word of the predicted word by word report as inputs into a decoder for report modeling, wherein an output of the decoder includes a location and content of text of a first text macro of the text macros associated with the context vector; and outputting the text of the first text macro associated with the context vector in the location of a report.

9. The computer program product of claim 8 wherein the operations further comprise augmenting the decoder output with a sentinel token, wherein the sentinel token indicates the first text macro associated with the context vector is to be inserted at the location in the report.

10. The computer program product of claim 9 wherein the operations further comprise producing a probability for the first text macro associated with the context vector to be inserted at the location in the report based upon, at least in part, the transcript, the first text macro associated with the context vector, and preceding words that precede the first text macro associated with the context vector in the report.

11. The computer program product of claim 10 wherein the probability for the first text macro associated with the context vector to be inserted at the location in the report is further based upon, at least in part, an encoded representation of an input to an encoder, and an encoded representation of the first text macro associated with the context vector.

12. The computer program product of claim 11 wherein the first text macro associated with the context vector for the report is displayed differently from non-text macro.

13. The computer program product of claim 11 wherein attributes of the first text macro associated with the context vector for the report are displayed differently from non-text macro.

14. The computer program product of claim 11 wherein any of the text macros is deleted from the report using a shortcut without requiring individual deletion of each character in content of the text macros.

15. A computing system including one or more processors and one or more memories configured to perform operations comprising:

encoding a transcript and text macros into vector representations;

predicting a word by word report based upon, at least in part, the encoding;

querying an attention mechanism based upon, at least in part, a decoder state;

producing an attention distribution over an encoder output of the encoding based upon, at least in part, the querying of the attention mechanism;

producing an interpolation of the encoder output as a context vector based upon, at least in part, the attention distribution;

inputting both the context vector and a predicted word of the predicted word by word report as inputs into a decoder for report modeling, wherein an output of the decoder includes a location and content of text of a first text macro of the text macros associated with the context vector; and outputting the text of the first text macro associated with the context vector in the location of a report.

16. The computing system of claim 15 wherein the operations further comprise augmenting the decoder output with a sentinel token, wherein the sentinel token indicates the first text macro associated with the context vector is to be inserted at the location in the report.

17. The computing system of claim 16 wherein the operations further comprise producing a probability for the first text macro associated with the context vector to be inserted at the location in the report based upon, at least in part, the transcript, the first text macro associated with the context vector, and preceding words that precede the first text macro associated with the context vector in the report.

18. The computing system of claim 17 wherein the probability for the first text macro associated with the context vector to be inserted at the location in the report is further based upon, at least in part, an encoded representation of an input to an encoder, and an encoded representation of the first text macro associated with the context vector.

19. The computing system of claim 18 wherein the first text macro associated with the context vector for the report is displayed differently from non-text macro and wherein attributes of the first text macro associated with the context vector for the report are displayed differently from non-text macro.

20. The computing system of claim 18 wherein any of the text macros is deleted from the report using a shortcut without requiring individual deletion of each character in content of the text macros.

* * * * *